US008309322B2

(12) United States Patent
Peters et al.

(10) Patent No.: US 8,309,322 B2
(45) Date of Patent: Nov. 13, 2012

(54) DITERPENE MODULATOR OF MACROPHAGE PHAGOSOMAL MATURATION

(75) Inventors: Reuben John Peters, Ames, IA (US); David G. Russell, Ithaca, NY (US); Francis M. Mann, Ames, IA (US)

(73) Assignees: Iowa State University Research Foundation, Inc., Ames, IA (US); Cornell University, Ithaca, NY (US)

( * ) Notice: Subject to any disclaimer, the term of this patent is extended or adjusted under 35 U.S.C. 154(b) by 264 days.

(21) Appl. No.: 12/776,759

(22) Filed: May 10, 2010

(65) Prior Publication Data

US 2010/0311818 A1 Dec. 9, 2010

Related U.S. Application Data

(60) Provisional application No. 61/184,173, filed on Jun. 4, 2009.

(51) Int. Cl.
*C12Q 1/18* (2006.01)
*A61P 31/06* (2006.01)

(52) U.S. Cl. .............. 435/32; 436/63; 424/9.1; 424/9.2; 514/44 R; 514/729; 536/23.1

(58) Field of Classification Search .................... 435/32; 424/9.1, 9.2; 436/63; 514/44 R, 729
See application file for complete search history.

(56) References Cited

OTHER PUBLICATIONS

Nakano, Chiaki et al., "Characterization of the Rv3377c Gene Product, a Type-B Diterpene Cyclase, from the *Mycobacterium tuburculosis* H37 Genome", ChemBioChem, 10:2060-2071 (2009).
Xu, Meimei et al., "Following evolution's lead to a single residue switch for diterpene synthase product outcome", PNAS, 104(18):7397-7401 (2007).
Nakano, Chiaki et al., "*Mycobacterium tuburculosis* H37Rv3377c encodes the diterpene cyclase for producing the halimane skeleton", Chem. Commun., 1016-1018 (2005).
Rudi, Amira et al., "Asmarines I, J, and K and Nozyberkol: Four New Compounds from the Marine Sponge *Raspailia* sp.", J. Nat. Prod., 67:1932-1935 (2004).
Nakano, Chiaki et al., "Structure of Diterpene Produced by Rv3378c Gene Product from *Mycobacterium tuberculosis*", Koryo, Terupen oyobi Seiyu Kagaku ni kansuru Toronkai Koen Yoshishu, 49:247-249 (2005).
Nakano, Chiaki et al., "4 Novel Halimane-type Diterpenes Produces by Pathogenic *Mycobacterium tuberculosis*: Molecular Cloning, Functional Analyses, Substrate Specificity and Biological Activity", Symposium on the chemistry of natural products, 48:19-24 (2006).

*Primary Examiner* — Savitha Rao
(74) *Attorney, Agent, or Firm* — McKee, Voorhees & Sease, P.L.C.

(57) ABSTRACT

Novel uses for diterpene modulators of macrophage phagosomal maturation are provided. The diterpene isotuberculosinol is used as an immune modulator, assay for pharmaceutical compositions and an isolated *Mycobacterium tuberculosis* labdane-related diterpenoid virulence factor. A method of treating *Mycobacterium tuberculosis* infectivity is further provided.

8 Claims, 11 Drawing Sheets

Halimadienyl diphosphate (1) Tuberculosinol (3)

Isotuberculosinol (2)

SEQUENCE LISTING

<160> NUMBER OF SEQ ID NOS: 4

<210> SEQ ID NO 1
<211> LENGTH: 295
<212> TYPE: PRT
<213> ORGANISM: Streptomyces griseus

<400> SEQUENCE: 1

Met Arg Ala Arg His Arg Val Ala Leu Lys Val Leu Ala Asp Leu Arg
1               5                   10                  15

Ser Trp Ala Ala Glu Tyr Pro Gln Val Leu Glu Ala Thr Pro Ile Glu
            20                  25                  30

Ala Leu Ala Ile Ser Thr Ala Ala Ile Ser Pro Trp Arg Gly Ala Asn
        35                  40                  45

Glu Leu Arg Leu Ser Ala Pro Asp Val Arg Cys Gly Pro Thr Pro Leu
    50                  55                  60

Asp Asp His Val Glu Gln Asn Val Arg Ser Leu Asp Glu Leu Asp Asp
65                  70                  75                  80

Leu Phe Gly Arg Cys Glu Ala Ile Val Arg Gly Gly Asp Arg Asp Asp
                85                  90                  95

Gly His Pro Leu Leu Ala Ser Leu Ser Gly Trp Gln Ser Ala Leu Glu
            100                 105                 110

Arg Ala Pro His Tyr Pro Lys Leu Ala Gly Leu Trp Gly Asp Arg Phe
        115                 120                 125

Ala Glu Ala Leu Arg Gly Glu Arg Tyr Asp Trp Thr Ala Gly Leu Ala
130                 135                 140

Arg Asp Arg Gly Glu Gly Pro Ser Asp Pro Gln Glu Tyr Leu Thr Tyr
145                 150                 155                 160

Ala Ala Ser Ser Asn Ala Trp Ile Thr His Phe Pro Arg Trp Ala Thr
                165                 170                 175

Ser Asp Arg Asp Asp Leu Leu Asp Gly Leu Pro Val Leu Asp Asn Ala
            180                 185                 190

Leu Glu Ala Ile Glu Val Ala Val Arg Leu Ser Asn Asp Leu Ala Thr
        195                 200                 205

Phe Glu Arg Glu Arg Ala Glu Pro Gly Gln Asn Asn Ile Leu Met Tyr
    210                 215                 220

Asp Thr Ser Pro Asp Trp Val His Asp Glu Leu Asp Arg His Ser Arg
225                 230                 235                 240

Lys Ala Gln Glu Gln Leu Asp Pro Leu Ala Thr Ala Gly Phe Pro Pro
                245                 250                 255

Ala Val Glu Leu Leu Arg Leu Leu Asp Trp Ser Val Thr Phe Tyr Ser

-continued

```
              260                 265                 270
Gly Ala Asp Phe Arg Gly Trp Gly Ser Asp Arg Asp Leu Thr Gly Pro
            275                 280                 285
Ser Gly Leu Pro Ser Asp Met
            290                 295

<210> SEQ ID NO 2
<211> LENGTH: 311
<212> TYPE: PRT
<213> ORGANISM: Streptomyces griseus

<400> SEQUENCE: 2

Met Pro Asp Ala Ile Glu Phe Glu His Glu Gly Arg Arg Asn Pro Asn
1               5                  10                  15
Ser Ala Glu Ala Glu Ser Ala Tyr Ser Ser Ile Ile Ala Ala Leu Asp
                20                  25                  30
Leu Gln Glu Ser Asp Tyr Ala Val Ile Ser Gly His Ser Arg Ile Val
            35                  40                  45
Gly Ala Ala Ala Leu Val Tyr Pro Asp Ala Asp Ala Glu Thr Leu Leu
        50                  55                  60
Ala Ala Ser Leu Trp Thr Ala Cys Leu Ile Val Asn Asp Asp Arg Trp
65                  70                  75                  80
Asp Tyr Val Gln Glu Asp Gly Gly Arg Leu Ala Pro Gly Glu Trp Phe
                85                  90                  95
Asp Gly Val Thr Glu Val Val Asp Thr Trp Arg Thr Ala Gly Pro Arg
            100                 105                 110
Leu Pro Asp Pro Phe Phe Glu Leu Val Arg Thr Thr Met Ser Arg Leu
        115                 120                 125
Asp Ala Ala Leu Gly Ala Glu Ala Ala Asp Glu Ile Gly His Glu Ile
    130                 135                 140
Lys Arg Ala Ile Thr Ala Met Lys Trp Glu Gly Val Trp Asn Glu Tyr
145                 150                 155                 160
Thr Lys Lys Thr Ser Leu Ala Thr Tyr Leu Ser Phe Arg Arg Gly Tyr
                165                 170                 175
Cys Thr Met Asp Val Gln Val Val Leu Asp Lys Trp Ile Asn Gly Gly
            180                 185                 190
Arg Ser Phe Ala Ala Leu Arg Asp Asp Pro Val Arg Arg Ala Ile Asp
        195                 200                 205
Asp Val Val Val Arg Phe Gly Cys Leu Ser Asn Asp Tyr Tyr Ser Trp
    210                 215                 220
Gly Arg Glu Lys Lys Ala Val Asp Lys Ser Asn Ala Val Arg Ile Leu
225                 230                 235                 240
Met Asp His Ala Gly Tyr Asp Glu Ser Thr Ala Leu Ala His Val Arg
                245                 250                 255
Asp Asp Cys Val Gln Ala Ile Thr Asp Leu Asp Cys Ile Glu Glu Ser
            260                 265                 270
Ile Lys Arg Ser Gly His Leu Gly Ser His Ala Gln Glu Leu Leu Asp
        275                 280                 285
Tyr Leu Ala Cys His Arg Pro Leu Ile Tyr Ala Ala Thr Trp Pro
    290                 295                 300
Thr Glu Thr Asn Arg Tyr Arg
305                 310

<210> SEQ ID NO 3
<211> LENGTH: 300
<212> TYPE: PRT
```

<213> ORGANISM: Bradyrhizobium japonicum

<400> SEQUENCE: 3

```
Met Ile Gln Thr Glu Arg Ala Val Gln Val Leu Glu Trp Gly Arg
1               5                   10                  15

Ser Leu Thr Gly Phe Ala Asp Glu His Ala Val Glu Ala Val Arg Gly
            20                  25                  30

Gly Gln Tyr Ile Leu Gln Arg Ile His Pro Ser Leu Arg Gly Thr Ser
            35                  40                  45

Ala Arg Thr Gly Arg Asp Pro Gln Asp Glu Thr Leu Ile Val Thr Phe
    50                  55                  60

Tyr Arg Glu Leu Ala Leu Leu Phe Trp Leu Asp Asp Cys Asn Asp Leu
65                  70                  75                  80

Gly Leu Ile Ser Pro Glu Gln Leu Ala Ala Val Glu Gln Ala Leu Gly
                85                  90                  95

Gln Gly Val Pro Cys Ala Leu Pro Gly Phe Glu Gly Cys Ala Val Leu
            100                 105                 110

Arg Ala Ser Leu Ala Thr Leu Ala Tyr Asp Arg Arg Asp Tyr Ala Gln
            115                 120                 125

Leu Leu Asp Asp Thr Arg Cys Tyr Ser Ala Ala Leu Arg Ala Gly His
    130                 135                 140

Ala Gln Ala Val Ala Ala Glu Arg Trp Ser Tyr Ala Glu Tyr Leu His
145                 150                 155                 160

Asn Gly Ile Asp Ser Ile Ala Tyr Ala Asn Val Phe Cys Cys Leu Ser
                165                 170                 175

Leu Leu Trp Gly Leu Asp Met Ala Thr Leu Arg Ala Arg Pro Ala Phe
            180                 185                 190

Arg Gln Val Leu Arg Leu Ile Ser Ala Ile Gly Arg Leu Gln Asn Asp
            195                 200                 205

Leu His Gly Cys Asp Lys Asp Arg Ser Ala Gly Glu Ala Asp Asn Ala
    210                 215                 220

Val Ile Leu Leu Leu Gln Arg Tyr Pro Ala Met Pro Val Val Glu Phe
225                 230                 235                 240

Leu Asn Asp Glu Leu Ala Gly His Thr Arg Met Leu His Arg Val Met
                245                 250                 255

Ala Glu Glu Arg Phe Pro Ala Pro Trp Gly Pro Leu Ile Glu Ala Met
            260                 265                 270

Ala Ala Ile Arg Val Gln Tyr Tyr Arg Thr Thr Ser Arg Tyr Arg
            275                 280                 285

Ser Asp Ala Val Arg Gly Gly Gln Arg Ala Pro Ala
    290                 295                 300
```

<210> SEQ ID NO 4
<211> LENGTH: 296
<212> TYPE: PRT
<213> ORGANISM: Artificial Sequence
<220> FEATURE:
<223> OTHER INFORMATION: Synthesized

<400> SEQUENCE: 4

```
Met Asn Leu Val Ser Glu Lys Glu Phe Leu Asp Leu Pro Leu Val Ser
1               5                   10                  15

Val Ala Glu Ile Val Arg Cys Arg Gly Pro Lys Val Ser Val Phe Pro
            20                  25                  30

Phe Asp Gly Thr Arg Arg Trp Phe His Leu Glu Cys Asn Pro Gln Tyr
            35                  40                  45
```

-continued

```
Asp Asp Tyr Gln Gln Ala Ala Leu Arg Gln Ser Ile Arg Ile Leu Lys
    50                  55                  60

Met Leu Phe Glu His Gly Ile Glu Thr Val Ile Ser Pro Ile Phe Ser
65                  70                  75                  80

Asp Asp Leu Leu Asp Arg Gly Asp Arg Tyr Ile Val Gln Ala Leu Glu
                85                  90                  95

Gly Met Ala Leu Leu Ala Asn Asp Glu Glu Ile Leu Ser Phe Tyr Lys
                100                 105                 110

Glu His Glu Val His Val Leu Phe Tyr Gly Asp Tyr Lys Lys Arg Leu
        115                 120                 125

Pro Ser Thr Ala Gln Gly Ala Ala Val Val Lys Ser Phe Asp Asp Leu
    130                 135                 140

Thr Ile Ser Thr Ser Ser Asn Thr Glu His Arg Leu Cys Phe Gly Val
145                 150                 155                 160

Phe Gly Asn Asp Ala Ala Glu Ser Val Ala Gln Phe Ser Ile Ser Trp
                165                 170                 175

Asn Glu Thr His Gly Lys Pro Pro Thr Arg Arg Glu Ile Ile Glu Gly
                180                 185                 190

Tyr Tyr Gly Glu Tyr Val Asp Lys Ala Asp Met Phe Ile Gly Phe Gly
        195                 200                 205

Arg Phe Ser Thr Phe Asp Phe Pro Leu Leu Ser Ser Gly Lys Thr Ser
        210                 215                 220

Leu Tyr Phe Thr Val Ala Pro Ser Tyr Tyr Met Thr Glu Thr Thr Leu
225                 230                 235                 240

Arg Arg Ile Leu Tyr Asp His Ile Tyr Leu Arg His Phe Arg Pro Lys
                245                 250                 255

Pro Asp Tyr Ser Ala Met Ser Ala Asp Gln Leu Asn Val Leu Arg Asn
            260                 265                 270

Arg Tyr Arg Ala Gln Pro Asp Arg Val Phe Gly Val Gly Cys Val His
        275                 280                 285

Asp Gly Ile Trp Phe Ala Glu Gly
    290                 295
```

DITERPENE MODULATOR OF MACROPHAGE PHAGOSOMAL MATURATION

CROSS-REFERENCE TO RELATED APPLICATIONS

This application is a nonprovisional application of U.S. Provisional Application No. 61/184,173, filed Jun. 4, 2009, which is herein incorporated by reference in its entirety.

GRANT REFERENCE

Work for this invention was funded in part by grants from the National Institute of Health Grant No. GM076324. The United States government may have certain rights in this invention.

FIELD OF THE INVENTION

The present invention relates generally to novel uses for diterpene compositions. The invention includes methods and biological reagents for improving immune cell function and methods of treating immune system disorders with the diterpene isotuberculosinol. The invention further includes assays for diterpene antagonists or inhibitors, assays, and methods of inhibiting pathogenicity of *Mycobacterium tuberculosis*.

BACKGROUND INFORMATION

*Mycobacterium tuberculosis* causes the contagious disease tuberculosis and has infected up to one-third of the global population and remains one of the leading causes of fatal infections. The disease is responsible for an estimated two million deaths annually. Drug resistant strains of *M tuberculosis* have been steadily increasing in frequency, posing an additional and more serious threat to public health. The bacterium enters and resides in its host cell macrophage by subverting phagosomal processing, such that following engulfment the resulting phagosome compartment remains at an early endosomal stage rather than maturing into a bactericidal phagolysosome. Several mechanisms have been proposed for this critical aspect of pathogenesis, and it seems certain that there are multiple means by which *M tuberculosis* prevents phagosomal maturation. As a result, *M. tuberculosis* remains a widespread and devastating human pathogen.

There is evidence that mycobacterial-specific cell surface lipids play a role in the arrest of phagosome maturation, evidence for other effectors is less definitive. Deretic et al., *Cell. Microbiol.* 8:719 (2006). Different genetic screens indicate roles for non-overlapping sets of genes. One screen focused on the primary effects early in the infection process and highlighted a role for the product of a five-gene operon nominally involved in isoprenoid biosynthesis, with mutations in the two unique/non-redundant genes (Rv3377c and Rv3378c) leading to a significantly decreased ability to prevent phagosomal maturation. Pethe et al., *Proc. Natl. Acad. Sci.,* 101(37):13642-13647 (2004).

Phagosomes containing wild-type *M tuberculosis* demonstrate an inability to acidify below pH 6.2. However, those containing the corresponding mutant mycobacteria acidified to pH 5.7, resulting in more than a three-fold increase in proton concentration causing a significant reduction in bacterial proliferation in macrophage cell culture. The fact that the mutants were among those with the most extreme phenotype, indicated that the product of the operon is required for *M tuberculosis* to attain full virulence and plays a role in the initial stages of *M tuberculosis* entry into macrophages. The enzyme encoded by the Rv3377c gene acts as a diterpene cyclase producing bicyclic halimadienyl diphosphate from the acyclic primary metabolite geranygeranyl diphosphate (GGPP) via a protonation-initiated (i.e., class II) cyclization mechanism. Nakano et al., *Chem Comm,* 2005:1016-1018 (2005).

The pathogenesis of various pathogens, such as *M. tuberculosis*, has led to research in the area of natural products including labdane-related diterpenoids. Labdane diterpenoids comprise a large group of approximately 7,000 known natural products defined as minimally containing the fused bicyclic hydrocarbon structure found in the labdane family of diterpenoids. The characteristic core structure results from the unusual biosynthetic origins of the compounds, uniquely initiated by a sequential pair of terpene synthase catalyzed reactions. Although a number of labdane diterpenoids exhibit medically relevant effects, including antibiotic, anti-inflammatory and anti-cancer activity, there remains a need for additional research in the area of novel labdane diterpenoids and the biological activity of diterpenoids for a variety of medically-relevant purposes, including the identification of virulence factors of known pathogens.

Therefore, it is an object of the present invention, to identify, isolate and characterize the diterpene virulence factor of *M tuberculosis*.

It is a further object of the present invention to develop compounds for use as immune modulators for *M tuberculosis* pathogens as well as immune system disorders, such as autoimmune diseases, allergies and other immune system conditions.

It is an additional object of the present invention to develop pharmaceutical compositions comprising the diterpene isotuberculosinol.

It is an additional object of the present invention to develop drug assays for compounds capable of inhibiting the production of the diterpene isotuberculosinol and/or terpene cyclases.

It is an additional object of the present invention to characterize a terpene cyclase to from *M. tuberculosis* capable of producing the diterpene virulence factor isotuberculosinol.

It is an additional object of the present invention to develop assay methods for the diterpene isotuberculosinol.

These and other objects of the invention will become more readily apparent from the following detailed description, examples and appended claims.

SUMMARY OF THE INVENTION

The present invention provides novel uses for the diterpene modulator of macrophage phagosomal maturation. Uses of the diterpene isotuberculosinol as a virulence factor and development of a pharmaceutical composition, due to its direct inhibition of phagosomal maturation are described. The present invention further provides methods of probing immune cell function and use of isotuberculosinol as a biological reagent for testing immune cell function. In addition, the invention provides assays for compounds capable of inhibiting the pathogenesis of *M. tuberculosis*.

DETAILED DESCRIPTION OF INVENTION

Figure 1:
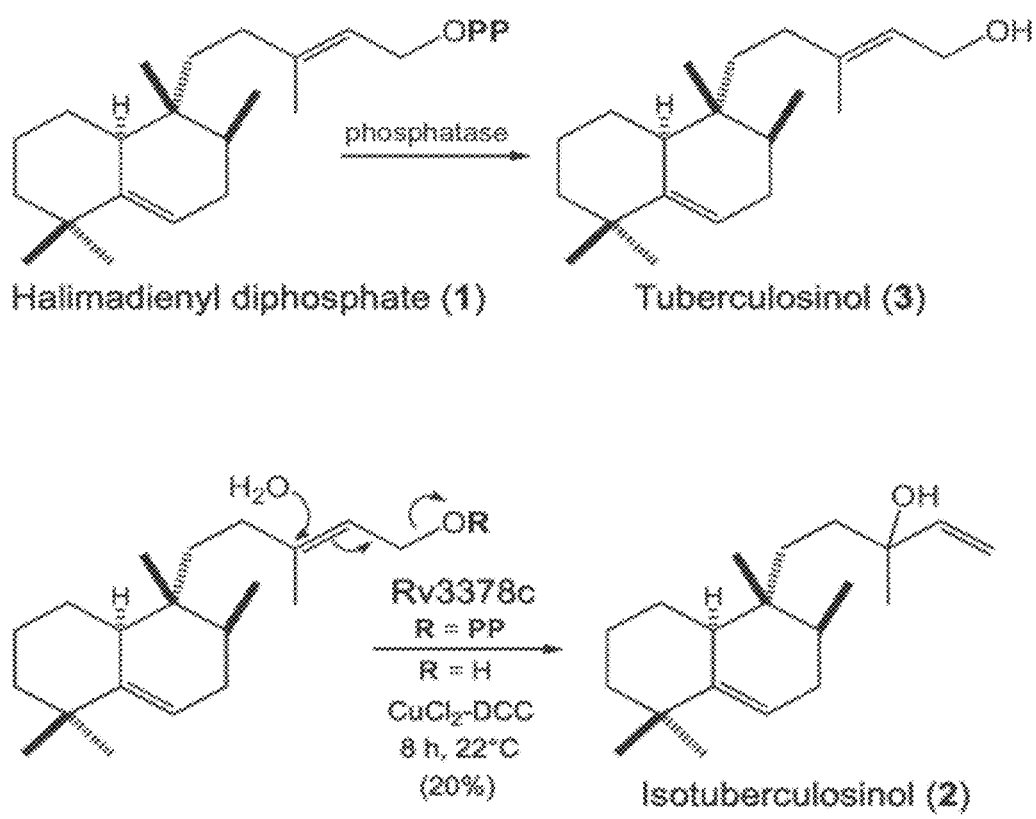
FIG. 1 demonstrates the cyclization of halimadienyl diphosphate to isotuberculosinol catalyzed by Rv3378c (Mt-EDS) and the corresponding biomimetic cyclization of tuberculosinal to isotuberculosinol.

The embodiments of this invention are not limited to particular compositions, assays or methods, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural references unless the context clearly indicates otherwise. Further, all units, prefixes, and symbols may be denoted in their SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation; the preferred materials and methods are described herein. In describing and claiming the embodiments of the present invention, the headings provided are not limitations on the embodiments of the invention and the following terminology will be used in accordance with the definitions set out below.

The pathogenesis of *M tuberculosis* includes the prevention of phagosomal maturation. Establishment of an infection requires *M tuberculosis* to halt endocytic maturation of the phagosome compartment created upon engulfment of the bacterium by macrophage cells of the human host immune system. There are multiple factors that contribute to the ability of *M tuberculosis* to initiate and maintain arrest of these phagosome compartments at an early endocytic stage. According to the present invention, one factor promoting the pathogen's arrest of phagosomal maturation is the diterpene isotuberculosinol. The structure of the diterpene isotuberculosinol was first reported as the single stereoisomer nosyberkol (isolated from the Nosy be Islands (Madagascar) sponge *Raspailia* sp.). Rudi, et al., *J. Nat. Prod.*, 67:1932-35 (2004). Subsequently, the isolation of a 1:1 mixture of tuberculosinol and nosyberkol (as a 3:1 mixture of stereoisomers) was identified as isotuberculosinol, by treatment of halimadienyl diphosphate with Rv3378c. Nakano, et al., *Koryo*, 49:247-249 (2005). However, the physiological effects of isotuberculosinol on phagosomal maturation were not identified.

According to the invention, isotuberculosinol alone arrests maturation of the endocytic phagosomal compartment at an early stage, a result similar to that observed upon engulfment of *M. tuberculosis* by macrophage cells of the mammalian immune system. According to the invention, various physiological uses for isotuberculosinol exist based on the diterpene's direct inhibition of phagosomal maturation in vitro and assisting of bacteria in evading the body's immune defenses in order to contribute to the early stage of the infection process of phagosomal arrest.

An embodiment of the invention includes use of the bioactive molecule isotuberculosinol for analysis and probing of immune cell function in subjects. According to an embodiment, the bioactive isotuberculosinol is administered to a subject or to cells in order to monitor and test the effects of phagosomal maturation in the subject or cells. Although the bioactive isotuberculosinol specifically arrests phagosome maturation, it does so in the macrophage in a non-cytotoxic manner, providing a non-cytotoxic manner of studying cell function of the immune system.

According to a further embodiment of the invention, the bioactive isotuberculosinol is utilized as a biological reagent for testing the immune cell function. As set forth in the examples, isotuberculosinol can be isolated, purified, and then stored for use as a biological reagent for immunology and molecular biology research to determine and further analyze immune cell function. Isotuberculosinol can be prepared as a reagent for convenient and efficient testing of biological samples. The biological reagent compositions of the present invention are particularly suitable for performing a wide variety of analytical procedures which are beneficially or necessarily performed for the testing of immune cell function, for example testing may be completed with blood plasma or diluted plasma.

The analysis of biological tissue samples is often a valuable diagnostic tool used by the pathologist to diagnose many illnesses and by the medical researcher to obtain information about a cell structure. Depending on the analysis or testing to be done with the isotuberculosinol reagent, a sample may undergo various preliminary steps, treatments or procedures prior to analysis, such as measurement of a variety of indicators of immune cell function as recognized by a skilled artisan with the benefit of the present disclosure. Typically the procedures are complex and time consuming, involving several tightly sequenced steps often utilizing expensive and toxic materials. According to the present invention, use of isotuberculosinol as a reagent composition may also comprise a plurality of additional reagents for testing immune cell function according to the invention.

The use of isotuberculosinol as a biological reagent specifically arrests phagosome maturation. However, according to the invention, it does so in the macrophage without killing the macrophage, making it a non-cytotoxic of studying cell function of the immune system. It is expected that a preferred reagent for testing immune cell function of biological samples will include use of bead based phagocytosis assays. Immune cell function may be analyzed according to the formation of a bead based isotuberculosinol reagent to determine the effect on a cell's phagosome formation with either control beads or beads coated in isotuberculosinol.

A further embodiment of the invention includes a pharmaceutical composition comprising isotuberculosinol and a carrier. According to the invention, isotuberculosinol impairs immune function by preventing proper immune processing through phagosomal maturation. Thus the invention also includes pharmaceutical preparations for humans and animals involving improperly functioning immune systems in need of treatment with isotuberculosinol. For example, pharmaceutical benefit exists for the use of the diterpene to treat conditions such as autoimmune disorders or allergies wherein the immune system improperly attacks the body, causing inflammation, and improper cell death. According to a further embodiment, pharmaceutical benefit exists for the use of the diterpene to treat diseases wherein which the immune system improperly breaks down tissues or cells. Use of isotuberculosinol for such exemplary conditions disables the improperly functioning immune system, providing beneficial pharmaceutical effects and promoting recovery of the immune system.

For administration, the isotuberculosinol can be combined with a pharmaceutically acceptable carrier. Pharmaceutical carriers are well known by those skilled in the art and may include for example, a suitable liquid vehicle or excipient and an optional auxiliary additive or additives as are all conventional and commercially available. The isotuberculosinol and pharmaceutically acceptable carrier can be formulated for a variety of means of delivery to a human or animal in need of treatment according to the invention. For example, as one skilled in the art will recognize, the pharmaceutical composition may be formulated for administration according to at least the following routes: parenteral, subcutaneous, intradermal, intramuscular, oral, intraperitoneal and inhalation administration Those skilled in the medical arts will readily appreciate that the doses and schedules of pharmaceutical composition will vary depending on the age, health, sex, size and weight of the human and animal. The amount will be a therapeutically effective amount, that is, an amount that will provide a therapeutic effect, to be determined in accordance with well-established medical practice. These parameters can be determined for each system by well-established procedures and analysis e.g., in phase I, II and III clinical trials and by review of the examples provided herein.

Similarly, according to an embodiment of the invention, the pharmaceutical composition is administered to a patient in need thereof for treatment of an immune disorder. Delivery of the pharmaceutical composition comprising isotuberculosinol and a carrier provides a mechanism of treating an improperly functioning immune system. The methods provide benefit for treating an autoimmune disorder, allergies or any other condition where the immune system improperly attacks the body or breaks down tissues or cells, often resulting in inflammation and/or improper cell death.

Accordingly, a further embodiment of the invention includes methods of inhibiting *M tuberculosis* infective processes. According to one embodiment of the invention, isotuberculosinol production by *M tuberculosis* is inhibited or decreased to minimize and/or inhibit pathogenicity of the bacterium. Regardless of the synthetic production of isotuberculosinol, the compound contributes to the suppression of phagosome maturation in the infection process of *M. tuberculosis* and provides a molecular target for biosynthetic inhibition of *M. tuberculosis* infection for development of anti-tuberculosis agents.

According to the invention, the arrest of phagosome maturation can be impacted through the unique and non-redundant genes Rv3377c and Rv3378c, having similar phenotypic consequences of mutation, which result in a significantly decreased ability to prevent phagosomal maturation. The gene Rv3377c encodes the known class II diterpene cyclase that catalyzed bicyclization and rearrangement of GGPP to halimadienyl diphosphate. The gene Rv3378c encodes a subsequently acting class I diterpene cyclase that synthesizes a diterpenoid from the product of Rv3377c. Rv3378c acts on halimadienyl diphosphate to further cyclize the halimadienyl diphosphate (enzyme termed MtEDS) and produces the natural diterpene product isotuberculosinol, as demonstrated and set forth in the examples (FIG. 1 (see 2)).

Rv3378c is annotated as encoding a hypothetical protein of unknown function and the translated sequence contains an aspartate-rich DDXXD divalent metal binding motif in common with enzymes catalyzing isoprenyl diphosphate ester cleavage and subsequent carbon-carbon bond formation in isoprenoid biosynthesis (i.e., isoprenoid diphosphate and class I terpene synthases). Christianson, *Chem. Rev.*, 106: 3412 (2006). Although the MtEDS contains the DDXXD motif, it does not exhibit any other homology to typical class I terpene synthases (i.e., MtEDS exhibits <10% overall amino acid sequence identity with any previously identified class I terpene synthase). Ikeda et al., *J. Biochem.*, 141:37-45 (2007); Dairi et al., *J. Bact.*, 183(20):6085 (2001); Hayashi et al., *J. Biochem.*, 141:37 (2007). Not intending to be bound to a single theory, homology remains a valid possibility, particularly given conservation of a $NDX_2SX_3E$ motif ~140 residues downstream of the previously noted DDXXD motif class I terpene synthases.

Figure 6:
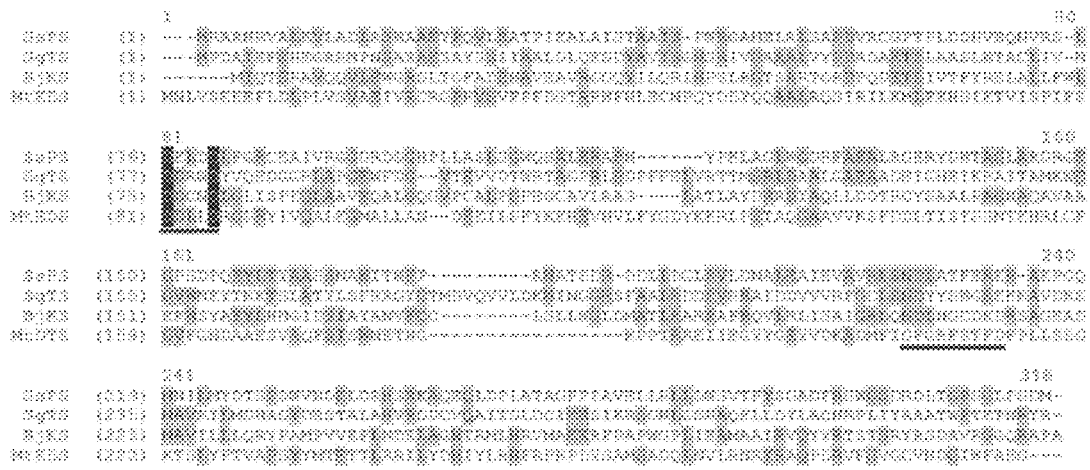
FIG. 6 demonstrates the alignment of MtEDS (SEQ ID NO:4) with other bacterial diterpene synthases: conserved DDXXD and otherwise conserved NDXX(S/T)XXXE motifs (underlined); SgTS (terpentetriene synthase from *Streptomyces grisea*) (SEQ ID NO:2); SsPS (pimaradiene synthase from *Streptomyces* sp. strain KO-39887) (SEQ ID NO:1); BjKS (kaurene synthase from *Bradyrhizobium japonicum*) (SEQ ID NO:3).
Figure 7:
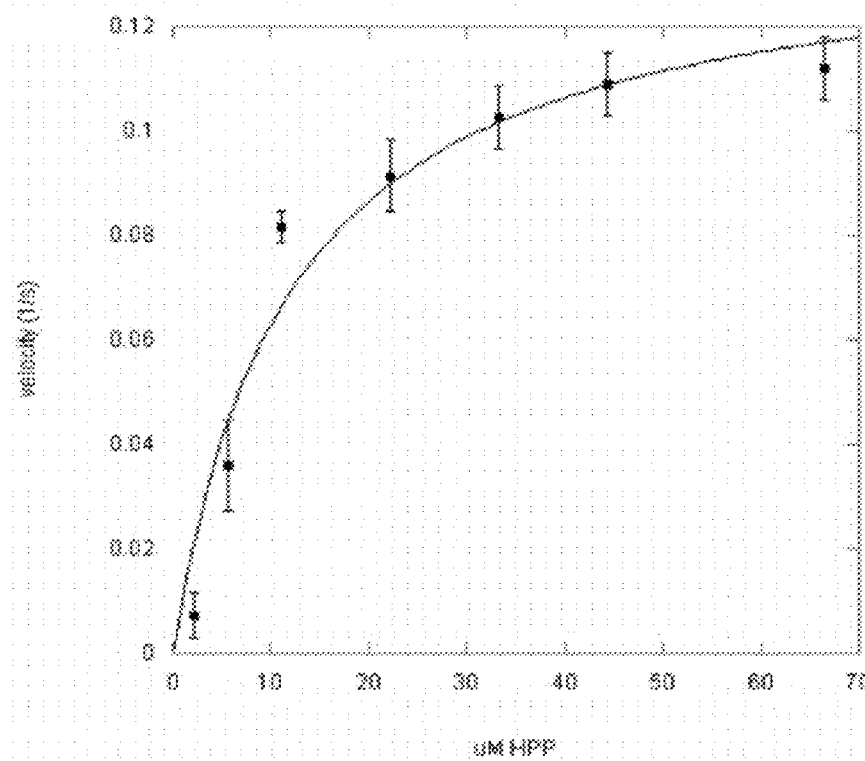
FIG. 7 demonstrates kinetic parameters of MtEDS in the presence of 10 mM $MnCl_2$. The apparent KM for HPP is 12 µM, and $k_{cat}$ is 0.13 $s^{-1}$ (catalytic efficiency is then $1.1 \times 10^4$ $s^{-1} M^{-1}$).

Structurally characterized class I terpene synthases are known to utilize both of these motifs in binding a catalytically requisite trinuclear divalent metal ion cluster, and mutational analysis has demonstrated that both motifs are critical for class I terpene synthase activity. Christianson, *Chem. Rev.*, 106:3412 (2006). However, MtEDS, in addition to the distinct lack of sequence identity/similarity to any other terpene synthase, bacterial or otherwise, does not contain the second NDX$_2$SX$_3$E divalent metal binding motif. (FIG. 6). Nevertheless, MtEDS exhibits catalytic efficiency equivalent to that of the other characterized bacterial class I diterpene synthase ($k_{cat}/K_M$=1.1×10$^4$ M$^{-1}$ s$^{-1}$), including reasonable affinity for its substrate ($K_M$=12 μM) (FIG. 7). In addition, mutational analysis demonstrates a catalytic role for the originally noted DDXXD motif, as alanine substitution for these asparates reduces catalytic activity 10$^2$-10$^4$ fold. (TABLE 1).

TABLE 1

| MtEDS Mutant | $k_{cat}$ (min$^{-1}$) | std |
| --- | --- | --- |
| Wt | 7.8 | 0.1 |
| D81A | 3.1 × 10$^{-4}$ | 2 × 10$^{-5}$ |
| D82A | 0.055 | 0.005 |
| D85A | 4.3 × 10$^{-4}$ | 4 × 10$^{-5}$ |

MtEDS is extremely divergent from other class I terpene synthases. According to the present invention, convergent evolution of MtEDS to class I terpene synthase activity, provides the unexpected result of forming isotuberculosinol from halimadienyl diphosphate (FIG. 1). Without being limited to any theory of evolutionary origin, the ability of isotuberculosinol to directly inhibit phagosomal maturation in the early infective steps of *M tuberculosis* makes the identification of the molecular target for isotuberculosinol and MtEDS desirable embodiments of the present invention.

According to an embodiment of the invention, inhibition of the class 1 diterpene cyclase MtEDS decreases and/or inhibits isotuberculosinol production. Therefore, according to the present invention, methods of inhibiting MtEDS directly inhibit phagosomal maturation in vitro and in vivo. Therefore, it is an embodiment of the invention to provide an immune system modulate for phagosomal maturation comprising a compound capable of decreasing or inhibiting synthesis of isotuberculosinol. According to a preferred embodiment, the immune modulator inhibits the enzymatic activity of MtEDS.

According to another embodiment of the present invention, use of the class II diterpene cyclase encoded by Rv3377c and highly unusual class I diterpene synthase encoded by Rv3378c (MtEDS) are directed to methods to produce drug targets against the *M tuberculosis* pathogen and assays for infectivity of pathogens. The relevant biological activity of isotuberculosinol indicates that the associated biosynthetic pathway provides an ideal target of pharmaceutical interest. For example, according to embodiments of the present invention, the virulence factor isotuberculosinol and MtHPS provide targets for novel antibiotic compositions. The biosynthetic pathway may be assayed to determine desirable pharmaceutical interventions and provide new drug target against the *M. tuberculosis* pathogen. Agents capable of inhibiting isotuberculosinol or inhibiting the biosynthetic pathway to produce isotuberculosinol are capable of treating the infectivity and decreasing the pathogenicity of the *M. tuberculosis* pathogen.

According to a further embodiment of the invention, alteration of Mg$^{2+}$ concentration to interfere with MtHPS activity represents a further mechanism for decreasing and/or inhibiting isotuberculosinol synthesis by infecting pathogens. Although not intending to be limited to a particular theory, according to the invention Mg$^{2+}$ concentration is a physiologically relevant biochemical mechanism responsible for triggering (or at least increases) isotuberculosinol biosynthesis upon phagosomal engulfment of the *M tuberculosis* pathogen.

Although not intending to be limited according to a particular theory, the exemplary use of HPS inhibitors provides mechanisms for inhibiting isotuberculosinol or inhibiting the biosynthetic pathway to produce isotuberculosinol. For example, the two related mechanism based transition state analogs (15-aza-14,15-dihydrogeranylgeranyl diphosphate and 15-aza-14,15-dihydrogeranylgeranyl thiolodiphosphate) demonstrate tight binding, providing a basis for pharmaceutical design against the biosynthetic pathway of producing isotuberculosinol. In addition, the plant class II diterpene cyclase inhibitor 15-azaGGPP is a tight binding inhibitor of MtHPS and can be modified to form a potent analog inhibitor by increasing stability and retaining affinity (see Examples below). Accordingly, it is an embodiment of the invention to use MtHPS and isotuberculosinol as drug targets.

According to a further embodiment of the present invention, the gene Rv3378c encodes for a terpene cyclase that produces the diterpene virulence factor isotuberculosinol. Production of isotuberculosinol provides a novel mechanism by which *M tuberculosis* manipulates the normal activity of its macrophage host cells, leading to establishment of a persistent infection with potentially fatal implications. Applicant's identification of the molecular target of *M tuberculosis*'s virulence factor isotuberculosinol is the first identification of a labdane-related diterpenoid implicated in pathogenic virulence. Accordingly, it is an embodiment of the invention to provide an immune system modulator that decreases and/or inhibits synthesis of isotuberculosinol. According to a preferred embodiment, the modulator inhibits enzymatic activity of the diterpene cyclase MtEDS.

Embodiments of the present invention further include methods for assaying drug candidate compositions capable of inhibiting cell infectivity caused by the pathogen *M tuberculosis*. The assay methods for drug candidates identify compounds capable of inhibiting in vivo infection by *M. tuberculosis* and include the introduction of cells to the pathogen, providing infected cells a compound and determining whether the compound inhibits the diterpene cyclases MtEDS and/or MtHPS in order to arrest synthesis of isotuberculosinol. Assays for compounds inhibiting isotuberculosinol production may include identification of diterpene cyclase antagonists or inhibitors.

An additional embodiment of the invention includes compounds identified by the assay methods for such intended drug candidates. Still further, additional embodiments include use of compounds capable of inhibiting isotuberculosinol for decreasing the infectivity and/or pathogenicity of *M. tuberculosis*.

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications to the embodiments of the invention to adapt it to various usages and conditions.

EXAMPLES

Example 1

The diterpene isotuberculosinol was structurally characterized by NMR. (TABLE 2).

TABLE 2

| Carbon Position | $\delta^{13}C$ (ppm) | $\delta^1H$ (ppm) |
|---|---|---|
| 1 | 27.53 | 1.894 (t) 14.0; 1.164 (t) 12.5 |
| 2 | 22.48 | 1.651 (m), 0.957 (m) |
| 3 | 41.15 | 1.481 (d) 12.4; 1.359 (t) 12.5 |
| 4 | 36.13 | |
| 5 | 145.80 | |
| 6 | 116.69 | 5.643 (m) |
| 7 | 31.84 | 1.920 (m) |
| 8 | 33.53 | 1.580 (m) |
| 9 | 36.14 | |
| 10 | 40.07 | 2.346 (t) 12.4 |
| 11 | 30.24 | 1.561 (m); 1.453 (m) |
| 12 | 35.35 | 1.549 (m); 1.473 (m) |
| 13 | 72.90 | |
| 14 | 145.60 | 5.871 (dd) 17.3, 10.8 |
| 15 | 111.49 | 5.273 (dd) 17.7, 4.2; 5.051 (d) 10.6 |
| 16 | 27.55 | 1.211 (s) |
| 17 | 15.20 | 0.909 (d) 7.1 |
| 18 | 29.97 | 1.239 (s) |
| 18 | 29.22 | 1.186 (s) |
| 20 | 16.42 | 0.806 (s) |

Structural Data: NMR spectra for the isotuberculosinol product were recorded at 25° C. on a Bruker Avance 700 equipped with a probe with cryogenic detection for $^1H$ and $^{13}C$. For 1D $^{13}C$ spectra 15 mM chromium (III) acetylacetonate was added to the sample as a relaxation enhancement agent. Structural analysis was undertaken using 1D $^1H$, 1D $^{13}C$, DQF-COSY, HSQC, multiplicity-edited HSQC, HMBC, HMQC-COSY and ROESY spectra acquired at 700 MHz using standard experimental protocols. In addition a ROESY spectrum was acquired at 10° C. Chemical shifts were referenced to TMS.

Example 2

Materials and Methods: Unless otherwise noted, all chemicals were obtained from Fisher Scientific (Loughborough, Leicestershire, UK) and molecular biology reagents from Invitrogen (Carlsbad, Calif., USA).

Construct Assembly Rv3377c and Rv3378c were cloned from *M. tuberculosis* strain H37Rv genomic DNA (USDA-NADC) based on public sequence information (Tuberculist, Pasteur Institute). Both genes were inserted into the Gateway expression system (pENTR), verified by complete sequencing, then transferred via directional recombination to pTH11, which results in expression as fusion proteins with the maltose binding protein (MBP) at the N-terminus.

Biosynthesis of Isotuberculosinol: Protein was expressed by growing cells to $OD_{600}$ of 0.8-1.0 and inducing with 0.5 mM IPTG for 16 hours, which yielded approximately 5 mg/L of protein. Cells were lysed via sonication on ice and the MBP tagged proteins purified over 1 mL bed volume of amylose resin as directed by the manufacturer (New England Biolabs, Ipswich, Mass., USA), but in the presence of 10 mM $MgCl_2$ for MBP-Rv3377c and 10 mM $MnCl_2$ for MBP-MtEDS. Geranylgeranyl diphosphate was obtained from Isoprenoids, LC (Tampa, Fla., USA) and converted to halimadienyl diphosphate (133 μM GGPP, 75 mM HEPES pH 6.8, 1 mM $MgCl_2$, 15 mM KCl, 10% Glycerol, and 250 μg MBP-Rv3377c). This reaction was incubated for 4 hours at 30° C. to ensure complete turnover. The resulting halimadienyl diphosphate was converted to isotuberculosinol by the addition of $MnCl_2$ to 10 mM and MBP-MtEDS (in 100 μg increments per hour for 10 hours). Final yield for the overall reaction was limited to 10-15% by competing nonenzymatic hydrolysis of the diphosphate to the corresponding primary alcohol tuberculosinol (as determined by comparison to control reactions without the addition of MBP-MtEDS). Isotuberculosinol was extracted from the reaction with hexane, the resulting organic solvent overlay removed, evaporated under nitrogen, resuspended in 50% acetonitrile (500 μg/mL), and purified over a C18 column via HPLC (1100 Series HPLC, Agilent Technologies, Santa Clara, Calif., USA). Product purity was analyzed via GC-MS using a VF-1 ms column with electrospray ionization mass spectrometry detection (Saturn 3900 Gas Chromatographer, Saturn 2100T Mass Spectrometer, Varian Industries, Palo Alto, Calif., USA).

Semi-synthesis of isotuberculosinol: Halimadienyl diphosphate was enzymatically produced as above. Tuberculosinol was generated by enzymatic dephosphorylation with Calf Intestinal Alkaline Phosphatase (NEB) in concentration of 100 U/mL, extracted with hexane, and dehydrated via a pseudourea intermediate. Majetich et al., *New J. Chem.,* 1999:129-131 (1999). Specifically, the hexane was removed by evaporation under nitrogen, the tuberculosinol dissolved in acetone, then stirred under nitrogen with 2 molar equivalents of dicyclohexylcarbo-diimide (DCC) in the presence of 0.1 molar equivalents of $CuCl_2$ for 4-8 hrs at room temperature. The resulting products were quantified by GC-FID, analyzed by GC-MS, then the produced isotuberculosinol purified as above and characterized by NMR to confirm equivalence to the enzymatic product.

Enzymatic Assays: MBP-MtEDS was purified as described above to ~90% purity and assessed for activity. Enzymatic activity was optimized at 100 nM enzymes for 5 minutes in the presence of 10 mM $MnCl_2$ or other divalent cation. The divalent cation was optimized via addition of 1, 5, or 10 mM of the relevant divalent cation to the reaction mixture described above. (FIG. 3). MtEDS was then added in 100-250 nM equivalents.

Due to the instability of MBP-MtEDS, it was not dialyzed, but all samples were tested against a 'negative' control or baseline divalent cation concentration of <0.25 mM $MnCl_2$. After determination of the optimal divalent cation ($Mn^{2+}$) and pH (7.5), purification was done in the presence of 10 mM $MnCl_2$. Assays were conducted in assay buffer containing 50 mM HEPES pH 7.5, 10% glycerol, 1 mM KCl, 10 mM $MnCl_2$, and concentrations of HPP ranging from 0.5 μM to 65 μM. Assays were conducted for 5 minutes and stopped with 110 μL of 20 mM N-ethyl-maleimide (NEM) and incubated for 5 minutes at 75° C. The excess NEM was neutralized with excess DTT. An internal standard of geranylgeraniol was inoculated into each individual culture at concentrations of 2.5 μg. The assay was then extracted three times with ~1 mL hexanes and dried under $N_2$ gas to complete dryness. The assay was then resuspended in 50 uL fresh hexanes and quantified via GC-FID by comparison of isotuberculosinol peak area to internal standard peak area. Curve fit was performed via Vector NTI Software (Invitrogen). For all curve fits $R^2$>90%.

Mutagenesis and Enzymatic Assays of MtEDS Mutants: Mutants of MtEDS were constructed via site directed mutagenesis of MtEDS/pENTR with single site mutant primers of approximately 18 bp. Mutants were confirmed via sequence analysis. The genes were then transferred to the pTH1 vector for expression as fusion to MBP as described above for wild-type MtEDS. The mutant enzymes also were purified as described above, and then assayed with 15 or 30 μM HPP and 1 μg enzyme for periods of 5 minutes, 30 minutes, 1 hour, or 24 hours. Assays were stopped, extracted, and quantified.

Example 3

Approximately 250 μg of the enzymatically generated diterpene was produced and purified. However, the Rv3378c encoded enzyme was found to be unstable in extended large-scale incubations. Although Applicant does not intend to be bound to a single theory, the catalyzed cyclization reaction of halimadienyl diphosphate to form isotuberculosinol may be due to the intrinsic reactivity of the halimadienyl structure itself. Therefore, a biomimetic synthetic chemical reaction was utilized to generate sufficient product for structural characterization.

The biomimetic reaction of pseudourea-mediated dehydration (Majetich et al., New J. Chem., 1999:129 (1999)) of the primary alcohol corresponding to hydrolytic dephosphorylation of halimadienyl diphosphate (MtEDS) (1) to tuberculosinol (2), is readily produced by enzymatic dephosphorylation of halimadienyl diphosphate (1) produced by GGPP by the Rv3377c encoded enzyme. The chemical reaction generated several diterpene olefins, including isotuberculosinol found in ~20% yield (by GC-MS analysis), providing a convenient semi-synthetic route for production of ~1 mg of pure compound. Additionally, extensive comparison of NMR spectra verified the equivalence of the semi-synthetically produced compound with the enzymatically generated diterpene.

This demonstrates that the unusual mechanism of isotuberculosinol formation from halimadienyl diphosphate reflects intrinsic reactivity of the substrate, rather than an enzymatically dictated complex reaction. While MtEDS clearly must catalyze diphosphate ester bond cleavage, the propensity of the resulting allylic carbocation to undergo the corresponding, otherwise unusual, cyclization reaction provides a straightforward chemical rationale consistent with the possibility of a unique convergent evolutionary origin for this enzymatic activity. The selective formation of isotuberculosinol arises from MtEDS binding the halimadienyl moiety in a conformation conducive to production of isotuberculosinol.

Example 4

Analysis of phagosomal maturation was performed employing ratio fluorescent measurements. In order to determine if isotuberculosinol is able to directly affect phagosomal maturation, pure compounds were tested in bead based phagocytosis assays. Yates & Russell, Methods Mol. Biol., 445:311 (2008). Phagosomal pH was measured with IgG-coated silica particles, labeled with the pH-sensitive fluorochrome carboxyfluorescein-SE. Yates et al., Traffic, 6 (2005). Phagosomal proteolysis was quantified with IgG-coated silica beads carrying the substrate DQ Green Bodipy BSA and the calibration fluorochrome Alexa 594. β-galactosidase activity was measured with IgG-opsonized, C18-silica beads coated in the substrate C12-fluorescein-digalactopyranoside and the calibration fluorochrome octadecyl rhodamine B.

The particles for measuring pH and proteolysis were complexed with de-fatted BSA and were loaded with isotuberculosinol by suspending the particles in 500 ml PBS in a sonicating water bath at 37° C. Isotuberculosinol (1-10 µg) in 5 µl hexane was added to the aqueous solution and sonicated for 2 min. The particles were washed and used immediately. Particles for measurement of β-galactosidase activity were loaded with isotuberculosinol through addition of the isoprenoid (1-10 µg) in hexane to the lipid suspension in $CHCl_3$ prior to evaporation of the solvent and rehydration of the particles in PBS in a sonicator water bath at 37° C. for 2 min. Particles were washed and used immediately.

Particle suspensions were adjusted to give a dose of approximately 3 particles per cell prior to addition to macrophage monolayers. Yates et al., Traffic, 8:241-250 (2007). The particles were bound for 3 min. at ambient temperature prior to washing and transfer to cuvettes in the environmental chamber of the PTI QM4 SE spectrofluorometer pre-equilibrated to 37° C. Measurements were acquired and processed. Cell viability was assessed at termination of all the assays through exclusion of the non-permeable dye Trypan Blue.

Figure 2A:
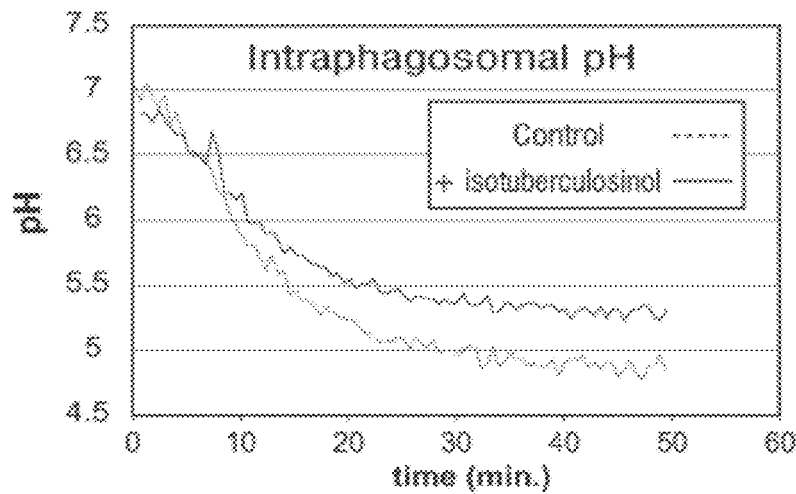
FIGS. 2A-C demonstrate the kinetics of phagosome maturation determined by ratio fluorometric measurements of (A) intraphagosomal pH (carbofluorescein), (B) intraphagosomal proteolytic activity (DQ Green protease substrate), and (C) intraphagosomal β-galactosidase activity (C12-fluorescein galactopyranoside) following bead uptake.
Figure 2B:
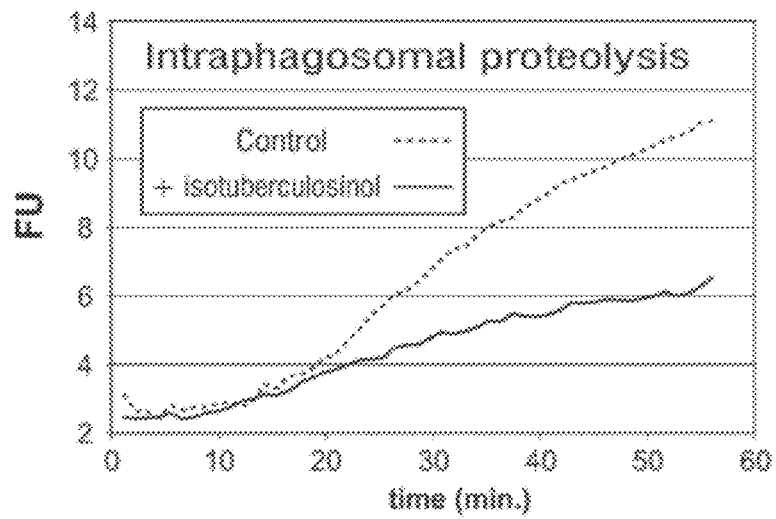
Figure 2C:
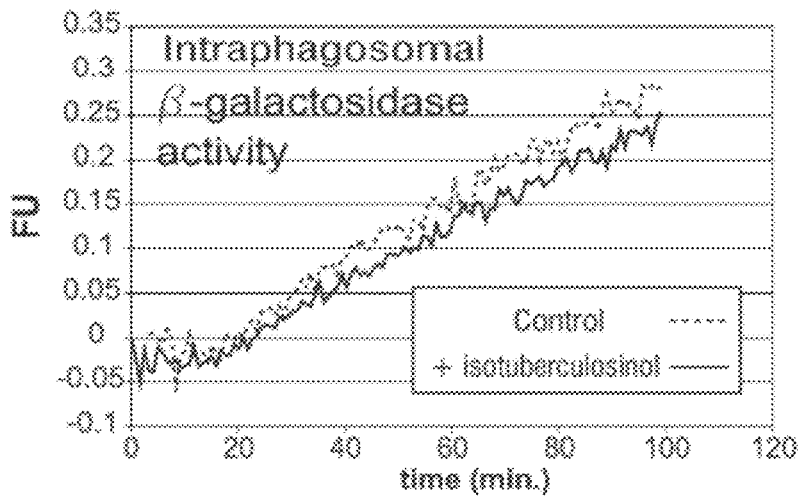
Figure 3:
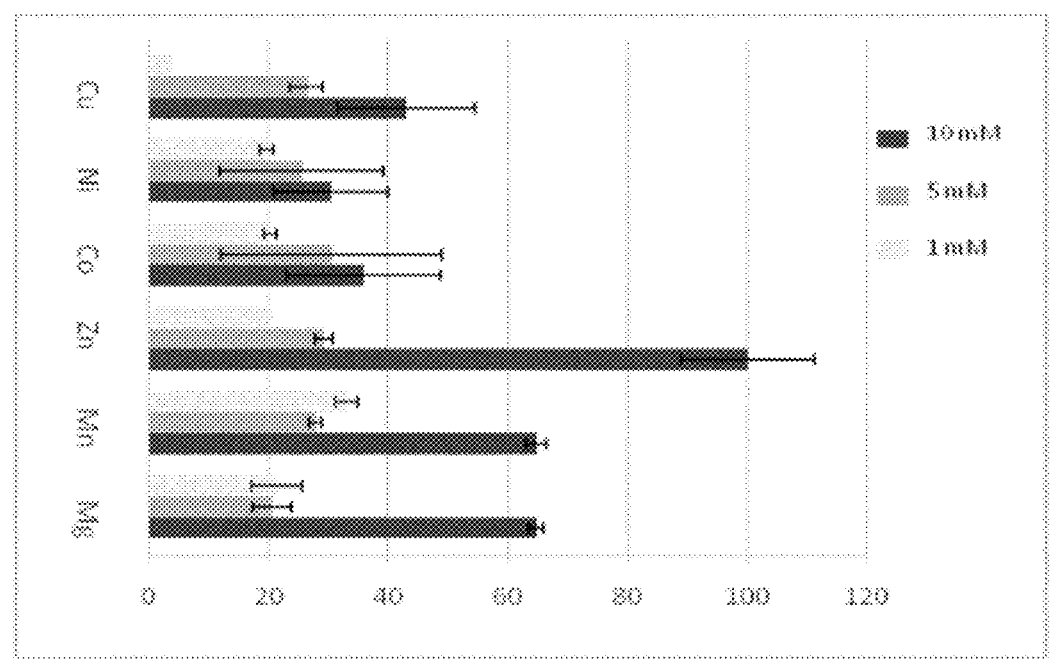
FIG. 3 demonstrates divalent cation optimization of MtEDS (relative rate). $Mn^{2+}$ performed slightly better than $Mg^{2+}$. Though $Zn^{2+}$ gave the most optimal activity, free $Zn^{2+}$ is not believed to be biologically relevant.
Figure 4A:
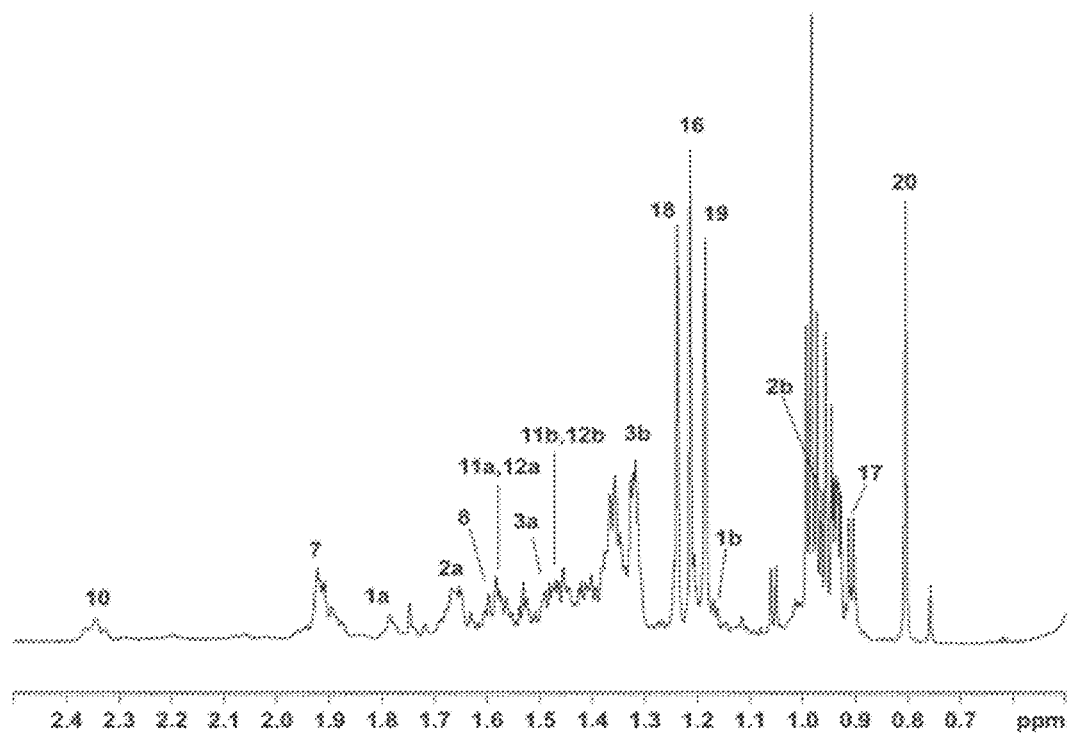
FIGS. 4A-B demonstrate (A) upfield region of $^1H$ NMR spectrum and (B) downfield region of $^1H$ NMR spectrum. 700 MHz $^1H$ NMR spectrum recorded in benzene-d6 at 25° C. Chemical shift assignments for overlapped regions were obtained from $^1H$-$^{13}C$ HSQC spectrum.
Figure 4B:
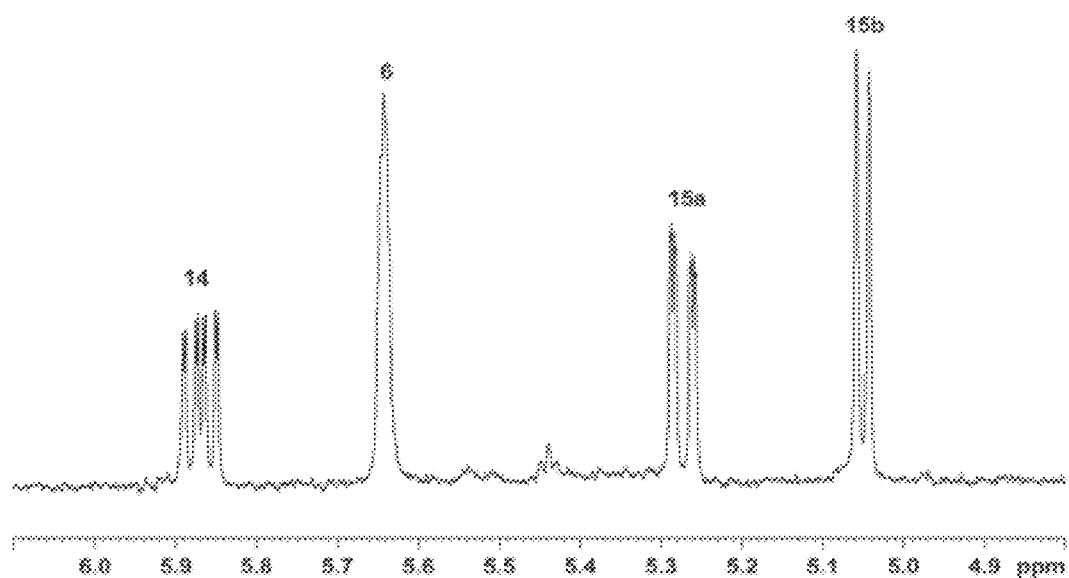
Figure 5A:
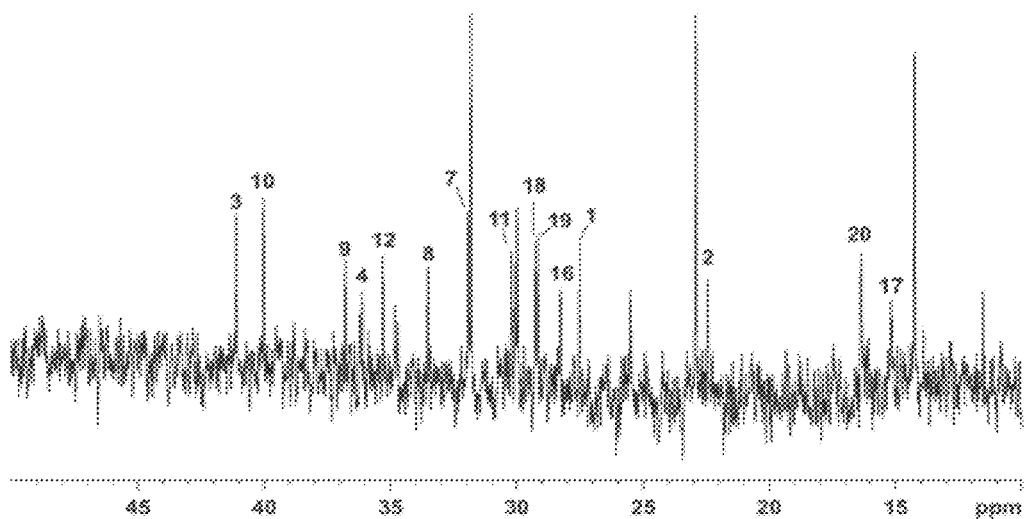
FIGS. 5A-B demonstrate (A) expanded upfield region and (B) full spectrum of $^{13}C$ NMR spectrum recorded in benzene-d6 at 25° C. with chromium (III) acetylacetonate added as a relaxation enhancement agent.
Figure 5B:
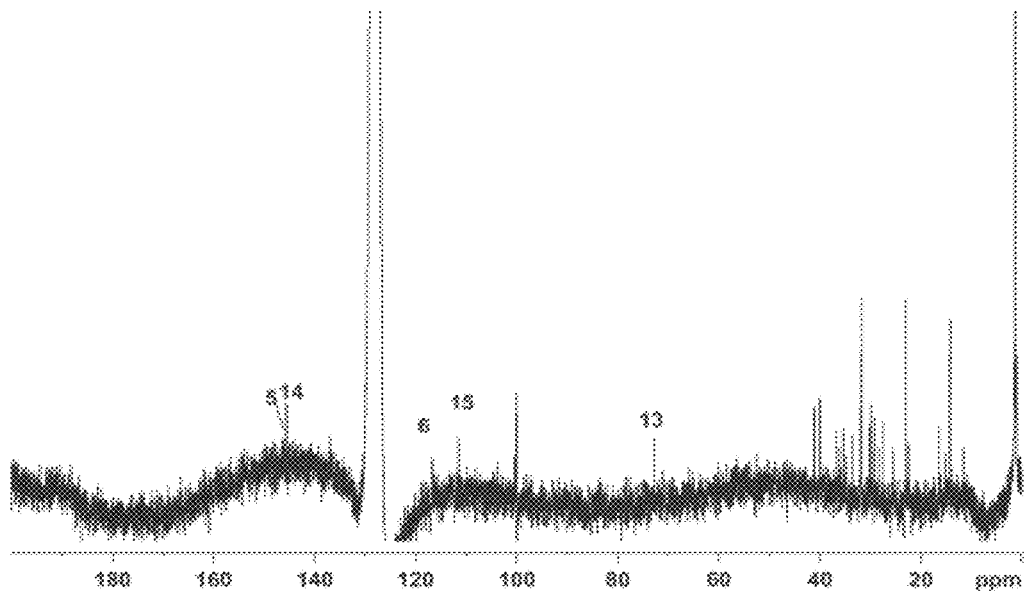

Phagosomes formed with control beads exhibited normal maturation, including full acidification to pH 4.8, as well as the acquisition of proteolytic and β-galactosidase activity. Beads coated with isotuberculosinol exhibited only partial maturation of their phagosome, with acidification arrested at pH 5.3 and a significant decrease in proteolytic activity. (FIGS. 2A-B). However, this was a selective rather than generally toxic effect, as little change in β-galactoside activity occurred (FIG. 2C), consistent with continued accessibility of M. tuberculosis-containing phagosomes to components of the early recycling endosomal system. Rohde et al. (2007). Isotuberculosinol's effect on acidification, an increased pH of ~0.5 units, is comparable to the effect of mutations in the Rv3377c and Rv3378c (MtEDS) genes on the pH of M tuberculosis-containing phagosomes, which were ~0.5 pH units more acidic than those containing wild type bacteria.

Example 5

As the ability of M tuberculosis to prevent phagosomal maturation after being engulfed is a critical early step in infection, the bacteria uses this modified organelle as the niche in which it persists and proliferates. Various mycobacterial species were compared, including M avium, M. smegmatis, M bovis and M tuberculosis to determine the effect of the isotuberculosinol operon on the infectivity and pathogenesis of the mycobacterium. Applicant tested the theory that isotuberculosinol is a factor contributing to the difference in infectivity between the mycobacterial species, to verify the role of the virulence factor at least in the initial stages of infection.

The non-pathogenic mycobacteria M avium and M smegmatis do not contain the isotuberculosinol operon. However, M bovis does contain a homologous sequence element with a frame shift in the gene corresponding to Rv3377c, which abrogates the activity of the encoded diterpene cyclase upon recombinant expression and, thus, it appears that M. bovis is not able to produce isotuberculosinol. M bovis is significantly less infectious (>100-fold) in humans than M. tuberculosis, requiring multiple bacteria for establishment of a productive infection relative to the single bacterium estimated for M. tuberculosis infection, despite the >99.9% identity between their genomes. Dannenberg, Mycobacteria: A Sourcebook, Vol. Part B:721 (1985); Garnier et al., Proc. Natl. Acad. Sci., 100:7877 (2003). This demonstrates that isotuberculosinol represents a key factor in the pronounced infectivity of M tuberculosis, and the corresponding biosynthetic machinery then represents a viable drug target.

Development of drug targets for isotuberculosinol's molecular target in the macrophage host cell focuses has significant uses for drug development. Use of diterpene synthases as antibiotic drug targets requires elucidation of the enzymatic mechanisms and finding inhibitors for the relevant diterpene synthases, similar to Applicant's related work with plant terpene synthases. Peters et al., J. Am. Chem. Soc., 123(37):8974-8978 (2001); Ravn et al., J. Am. Chem. Soc., 124(24):6998-7006 (2002); Roy et al., J. Am. Chem. Soc., 129:12453-12460 (2007).

Characterization of HPS from M bovis: In examining the M bovis HPS homolog, we noticed that this gene (Mb3411c/MbHPS) is annotated as having a 3 by for 4 by frame-shifting substitution (CAAT→AAC) towards its 3' end (~nucleotide 1220) in the reported genome sequences for M bovis, both strain AF2122/97 and the vaccination strain *bacillus* Calmette-Guérin (BCG) Pasteur 1173P2. Upon cloning MbHPS from *M. bovis* strain 95-1315 we confirmed this frame shift mutation, which leads to a change in C-terminal sequence relative to the last 95 amino acid residues found in MtHPS, including early termination after 483, instead of 501, residues. To determine if this was sufficient to abrogate enzymatic activity, MbHPS was expressed as an MBP fusion protein using the same protocols used with MtHPS, which led to readily apparent expression of MBP-MbHPS, albeit with the expected smaller apparent size relative to MBPMtHPS, upon SDS-PAGE analysis. However, the MBP-MbHPS construct did not exhibit activity, with no conversion of GGPP to HPP found even upon extended incubations (up to 72 hours) in the optimized assay conditions using either recombinant cell-free extracts or large amounts of pure enzyme.

HPS, and correspondingly isotuberculosinol biosynthetic capacity, are conserved in *M tuberculosis*, but not in other mycobacteria, including M bovis (containing the corresponding biosynthetic operon). HPS is conserved in all four *M. tuberculosis* strains with corresponding sequence information available (H37Rv, Haarlem, F11, and C), in the sequenced *M. bovis* strains AF2122/97 and BCG Pasteur 1173P2, as well as the 95-1315 strain used here. The MbHPS homolog carries a frame-shifting mutation that appears to abrogate its enzymatic activity and, hence, isotuberculosinol biosynthesis in M bovis. Notably, despite sharing more than 99.9% genomic sequence identity, M bovis appears to be less infectious in humans than *M tuberculosis*, and is a significantly less common causative agent of tuberculosis. Kumar et al., Robbins Basic Pathology, 8th ed. (2007). Such loss of isotuberculosinol production is a factor contributing to the reduced infectivity and/or virulence of *M. bovis*. A role in infectivity would be consistent with the design of the initial genetic screen that identified the isotuberculosinol operon, which selected for factors playing a role in very early stages of infection, as well as the activity of isotuberculosinol itself, as indicated by both mutant phenotype and its rapid (within 20 min) effect on phagosome maturation in isolation.

Example 6

The characterization of the class II diterpene cyclase that catalyzes the committed step in isotuberculosinol biosynthesis is halimadiene diphosphate synthase (HPS; EC 5.5.1.16). Kinetic analysis suggests a potential biochemical regulatory mechanism that triggers isotuberculosinol production upon phagosomal engulfment. Additionally, characterization of potential HPS inhibitors is provided. Two related mechanism based transition state analogs (15-aza-14,15-dihydrogeranylgeranyl diphosphate and 15-aza-14,15-dihydrogeranylgeranyl thiolodiphosphate) exhibit very tight binding, providing a basis for pharmaceutical design against the biosynthetic pathway of producing isotuberculosinol.

Initial functional characterization of HPS was limited by enzymatic instability. Here the development of a construct amendable to kinetic characterization is set forth, along with the implications of the observed striking Mg2+ co-factor inhibition effect, in addition to analysis of potential inhibitors, with two mechanism-based transition state analogs found to exhibit high affinity.

Experimental Procedures: Unless otherwise stated, molecular biology reagents were purchased from Invitrogen (Carlsbad, Calif.) and chemicals from Fisher Scientific (Pittsburgh, Pa.). Gas chromatography (GC) with flame ionization detection (FID) was carried out using an Agilent (Santa Clara, Calif.) 6890N GC, and with mass spectral detection (MS) using a Varian (Palo Alto, Calif.) 3900 GC with Saturn 2100 ion trap MS.

Cloning: HPS was cloned from genomic DNA from both *M tuberculosis* strain H37Rv and M bovis strain 95-1315. Both were inserted into the Gateway expression system (pENTR), and verified by complete sequencing, then transferred via directional recombination into expression vectors.

Protein Expression:. MtHPS was transferred into six different expression vectors to optimize (fusion) protein expression. These vectors included pDEST14 (no tag/fusion), pDEST15 (Glutathione-S-transferase), pDEST17 (6×His), pTh8 (Thioredoxin), pTH1 (Maltose Binding Protein; MBP), and pRW1 (Thioredoxin-His patch), with all fusions protein tags expressed N terminal to MtHPS. These vectors were individually transformed into *E. coli* strain C41 (Lucigen, Middleton, Wis.) and grown in NZY media at 37° C. to an OD of 0.6-0.8 at $A_{600}$. The temperature was then dropped to 16° C. for 1 hour, and the cells induced with 0.5 mM IPTG and cultured for an additional-16 hours. Cells were removed from media by centrifugation and resuspended in 1/50th of the culture volume lysis buffer (10 mM Tris-C1, 10% glycerol, 10 mM $MgCl_2$, 1 mM DTT, pH 6.8). Cells were lysed by brief sonification and clarified via centrifugation.

Detection of enzymatic activity: Initial analysis of HPS activity was carried out with clarified cell extracts. Assays were conducted with an assay buffer consisting of 10 mM HEPES (pH 7.75), 10% glycerol, 1 mM $MgCl_2$, 10 mM KCl. To 0.9 ml of assay buffer 0.1 ml of clarified lysate was added, and the assays then initiated by addition of GGPP to a final concentration of 5 μM. After incubation at 30° C. for 1 hour, the substrate (GGPP) and any resulting product (HPP) were enzymatically dephosphorylated to the corresponding alcohol using 10 units of Calf Intestinal Alkaline Phosphatase (New England Biolabs, Ipswich, Mass.), which was allowed to incubate 14-16 hours at 37° C. The diterpene alcohols were then extracted from the aqueous assay buffer via three successive 1 ml co-incubations with hexanes. The hexanes were then dried to completion and the diterpene alcohol was brought up in 50 μL of fresh hexanes for GC-MS analysis.

Protein purification: Clarified extracts from MBP-HPS expressing cells were mixed with 3 ml of a slurry (50% wt/vol) of Amylose resin (New England Biolabs, Ipswich, Mass.) and Maltose Binding Protein (MBP) buffer (50 mM $NaHPO_4$, 10 mM $MgCl_2$, 300 mM NaCl, pH 6.8) and incubated for 2 hours. The resin was washed with 3 successive washes of 15 ml MBP buffer before eluting with MBP buffer containing 50 mM Maltose. The resulting MBP-HPS was estimated to be ~95% pure by SDS-PAGE analysis. This purified protein was dialyzed in 25 kD molecular weight cut-off membrane (Spectrum Chemical and Laboratory Products, Gardena, Calif.) against dialysis buffer 1 (50 mM $NaHPO_4$, 300 mM NaCl, 10% glycerol, 1 mM DTT, 100 mM EDTA, pH 7.4) for 16 hours, and then dialyzed for two 45-min periods against dialysis buffer 2 (same as dialysis buffer 1, but without EDTA). The resulting pure MBP-HSP was assayed immediately, as freezing leads to loss of ~10% activity over the course of a week, although preparations stored at 4° C. for <24 hours retained essentially full activity.

Kinetic analyses: The enzymatic concentration and assay time were iteratively optimized for kinetic analysis with purified MBP-HPS (from *M. tuberculosis*), resulting in the selection of 25 nM enzyme and 1 min., respectively. 1 ml assays were carried out. Briefly, enzymatic activity was quenched via the addition of 110 μL of 20 mM N-ethyl-maleimide and incubation at 75° C. for 5 minutes. The remaining N-ethylmaleimide was neutralized with 20 mM DTT prior to dephosphorylation and extraction of the resulting alcohols, carried out as described above. All measurements for kinetic analysis were carried out via GC-FID analysis of the fractional conversion of substrate to product, as previously described, with triplicate assays run for each reported data point. Divalent cation dependence was measured by replacing the 1 mM MgCl$_2$ in the assay buffer with 0.1, 1, or 10 mM of various divalent cation salts. More detailed analysis was carried for the optimal Mg$^{2+}$, using concentrations ranging from 0.001 to 10 mM. Assays were then carried out at the optimal 0.1 mM Mg$^{2+}$ concentration using GGPP concentrations ranging from 1 to 100 µM.

Synthesis of Aza Analog Inhibitors: (FIG. 8 (see 7a and 7b) 15-AzaGGOH (6a) was prepared in four steps from 14,15-epoxy-GGOH epoxide hydrolysis to the 14,15 diol, periodate cleavage, reductive amination with Me$_2$NH (NaBH$_3$CN, MeOH), and acetate hydrolysis. Conversion to the mixed monophosphate (C1P(O)(OEt)$_2$, pyr, CH$_2$Cl$_2$, 0° C.) and displacement with (BuN$_4$)$_3$HOPP (CH$_3$CN, mol sieves, room temp, 5 days) followed by ion exchange, cellulose chromatography, lyophilization, and preparative HPLC afforded 15-azaGGPP. Conversion of 15-azaGGOH to the corresponding methanesulfonate (6c, CH$_3$SO$_2$Cl and EtsN in CH$_3$CN at −30° C., 30 min) followed by reaction with (Bu$_4$N)$_3$SPP (15) and molecular sieves (0° C., 1 h) modeled after a procedure for preparation of GGSPP by Phan and Poulter gave 15-azaGGSPP (7b, 46 mg, 85%) following ion exchange, centrifugation-extractions with MeOH, and flash chromatography on cellulose. Assays with these inhibitors were carried out with 5 min pre-incubation of the inhibitor with 50 nM MBP-MtHPS prior to addition of GGPP (to 5 µM) to initiate 3 min reactions.

Results

Figure 8:
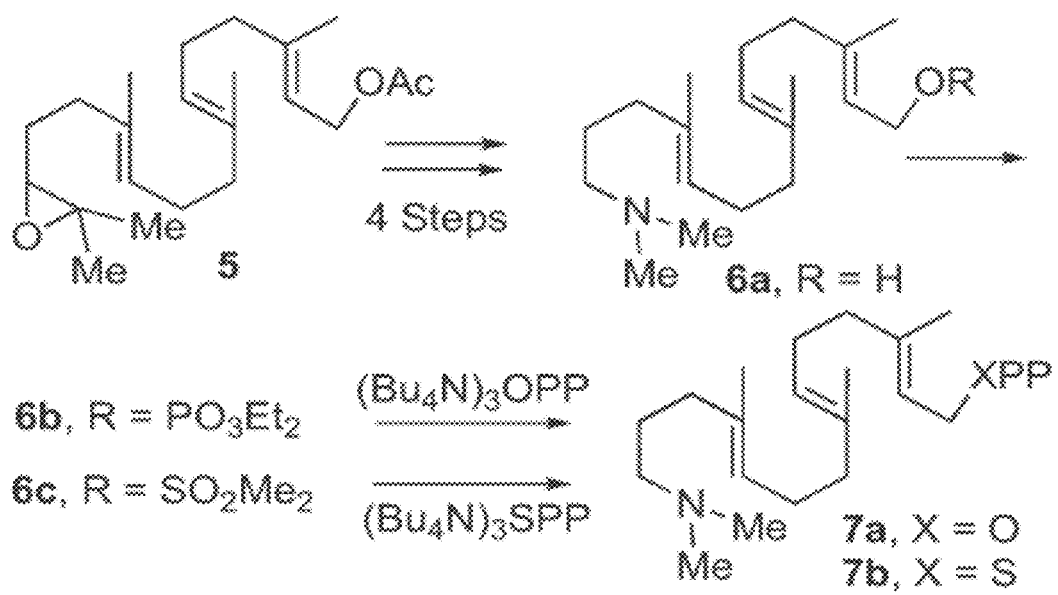
FIG. 8 demonstrates the chemical syntheses of aza analog inhibitors 15-azaGGPP (7a) and 15-azaGGSPP (7b) from 14,15-epoxyGGOH (5) via a common 15-azaGGOH intermediate (6a).
Figure 9A:
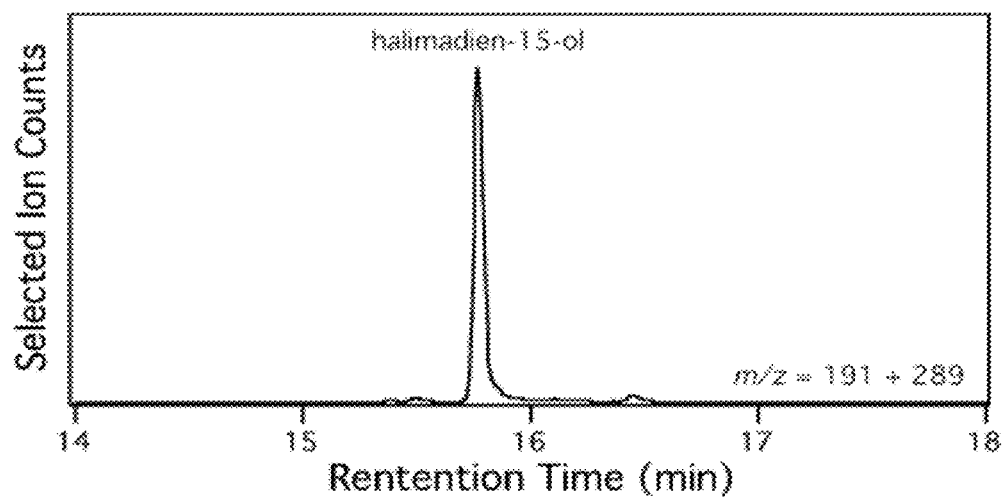
FIGS. 9A-B demonstrate MBP-MtHPS mediated conversion of GGPP to HPP showing: (A) selected ion chromatogram from GCMS analysis of halimadien-15-ol resulting from dephosphorylation of the HPP produced by purified MBP-MtHPS from GGPP; (B) mass spectra of halimadien-15-ol.
Figure 9B:
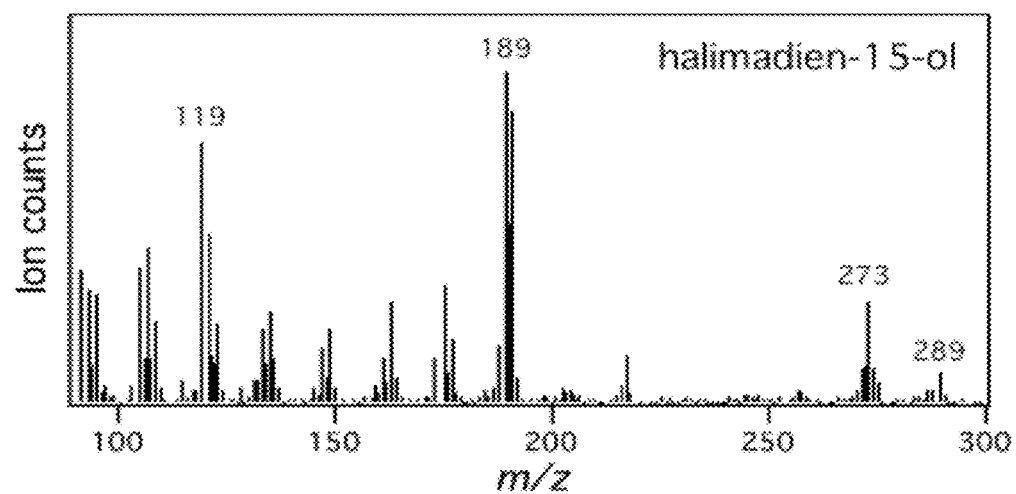

HPS expression construct: In the initial functional characterization report it was noted that HPS was difficult to express recombinantly, requiring co-expression of the GroEL protein folding chaperone. Consistent with this, upon cloning the corresponding gene (Rv3377c/MtHPS) from *M tuberculosis* (strain H37Rv), we found that recombinant expression only resulted in activity when MtHPS was fused to the maltose binding protein (MBP), although several other fusion proteins were also assessed. The resulting MBPMtHPS protein was able to convert GGPP to HPP completely, as determined by comparison of spectral measurements of the hydrolytically dephosphorylated alcohol to those previously reported, wherein this compound was termed tuberculosinol (halimadien-15-ol). Notably, while initial assays were carried out with cell-free extracts, the presence of the MBP tag enabled rapid purification, with the purified MBP-MtHPS similarly able to convert GGPP to HPP completely (FIG. 8).

Figure 10:
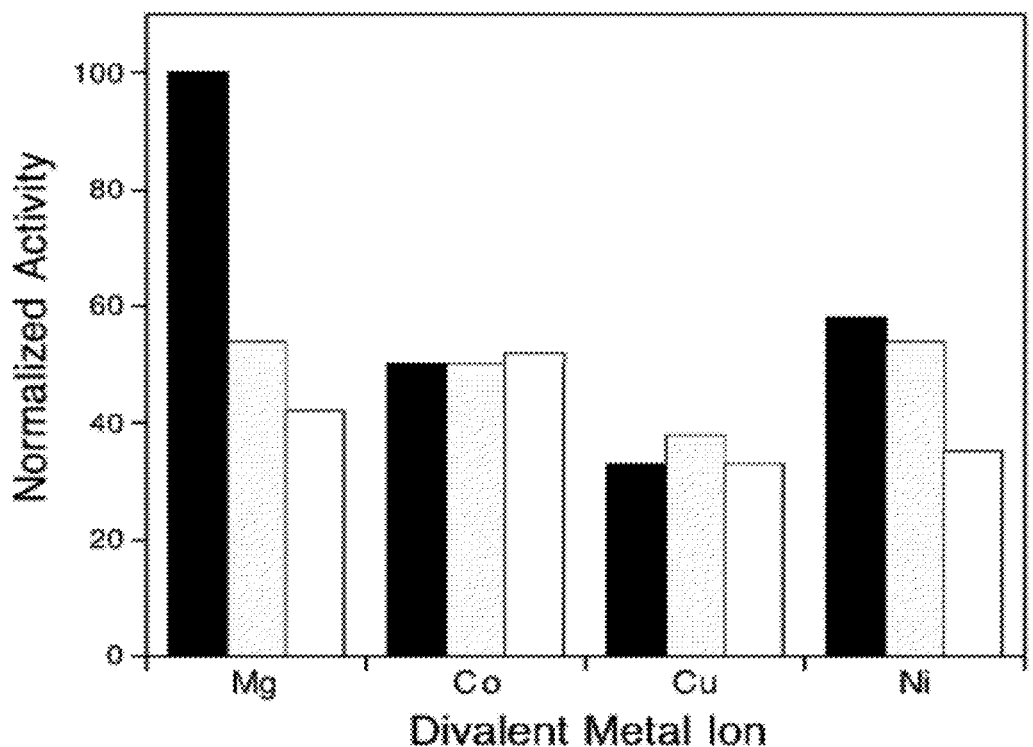
FIG. 10 demonstrates the relative MBP-MtHPS activity with various divalent metal ion co-factors (as identified, with 0.1, 1, and 10 mM concentrations indicated by solid, shaded, and open bars, respectively).

Magnesium co-factor dependence: As with other characterized class II diterpene cyclases, it was found in the initial characterization report that MtHPS requires Mg$^{2+}$ as an enzymatic co-factor. After optimization of the assay for kinetic measurements, the ability of a variety of divalent cations to support MtHPS activity at various concentrations (0.1, 1, and 10 mM) was investigated. This included Mg$^{2+}$, Co$^{2+}$, Cu$^{2+}$, Fe$^{2+}$, Mn$^{2+}$, Ca$^{2+}$, and Zn$^{2+}$, although due to interference with the secondary enzyme in our coupled assay (phosphatase), we were unable to measure kinetic rates with Mn$^{2+}$ and Zn$^{2+}$. Of the remaining divalent cations, MtHPS reacted most efficiently in the presence of low levels of Mg$^{2+}$ (FIG. 10).

The decrease in activity observed with higher levels of divalent cations indicates that MtHPS undergoes substrate-like co-factor inhibition, much as been reported with plant class II diterpene cyclases. This was more closely investigated with a detailed analysis of Mg$^{2+}$-dependence (FIG. 11), demonstrating that MtHPS is most active in the presence of 0.1 mM Mg$^{2+}$, and displays a rapid loss of activity as the concentration is raised above this point (e.g., >50% loss at 0.5 mM).

Figure 12:
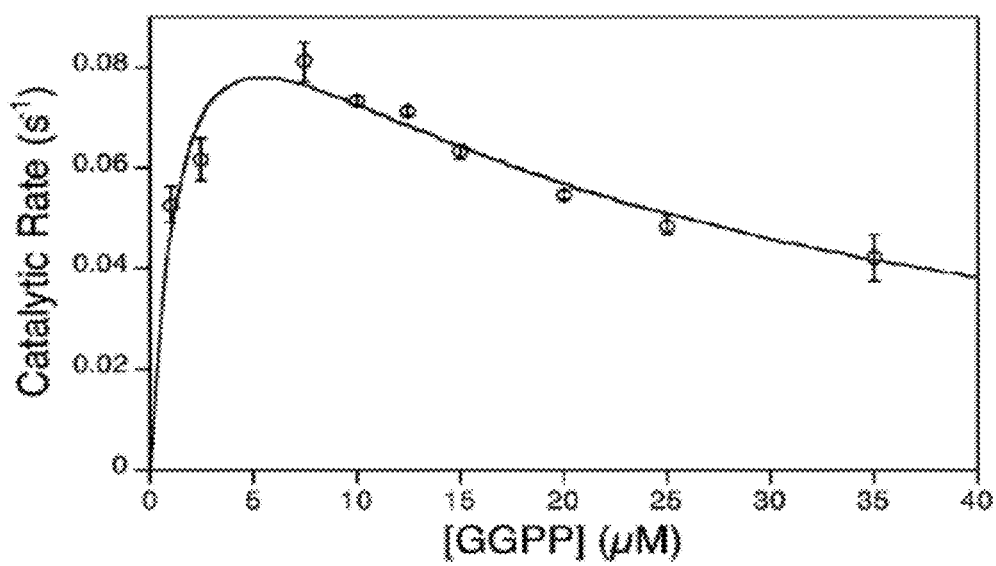
FIG. 12 demonstrates kinetic analysis of MBP-HPS activity.

Kinetic analysis: Substrate inhibition effects with GGPP also have been previously reported for some, although not all, class II diterpene cyclases. Prisic et al., *Plant Physiol.*, 144:445-454 (2007); Hamano et al., *J. Biol. Chem.*, 277:37098-37104 (2002); Ikeda et al. (2007); Peters et al., Biochemistry, 39:15592-15602 (2000); Hayashi et al., *Biosci. Biotechnol. Biochem*,. 72:523-530 (2008); Kawaide et al., *J. Biol. Chem.*, 275:2276-2280 (2000). Upon kinetic analysis of the GGPP concentration dependence of MtHPS activity a clear substrate inhibition effect was observed, with an apparent KM of 1.6±0.6 µM, an apparent Ki of 18±6 and kcat of 0.12±0.2 s$^{-1}$ (FIG. 12).

Figure 13:
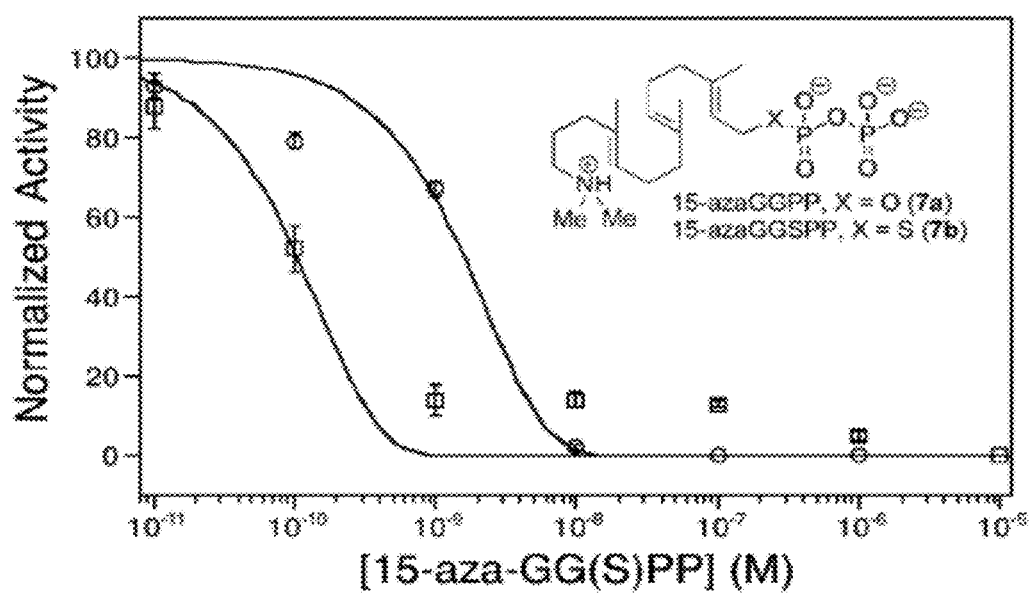
FIG. 13 demonstrates the inhibition of MBP-MtHPS: 15-azaGGPP (□); 15-azaGGSPP (○), with structures shown (inset).

Inhibition of HPS: It has been previously shown that 15-aza-14,15-dihydrogeranylgeranyl diphosphate (15-azaGGPP, 7a), an analog of the high energy intermediate formed by protonation of the terminal carbon-carbon double bond of GGPP (the initial step in class II cyclization), is a potent inhibitor of a plant diterpene synthase, a bietadiene synthase, with class II diterpene cyclase activity. Thus, the ability of 15-azaGGPP to inhibit MtHPS activity was investigated here, with an observed IC$_{50}$ of 0.1 nM. In addition, the potentially more stable thiolo analog, 15-aza-14,15-dihydrogeranylgeranyl thiolodiphosphate (15-azaGGSPP, 7b), proved to be a similarly potent inhibitor, exhibiting an IC$_{50}$ of 2 nM (FIG. 13), despite the larger size of the sulfur atom, the longer C—S and S—P bonds, and presumably diminished affinity for the Mg$^{2+}$ cofactor. Notably, given that these assays were performed with 50 nM enzyme, the resulting relatively very low IC$_{50}$ values indicate that only a small fraction of MBP-MtHPS is correctly folded (i.e., active and able to bind these inhibitors). Nevertheless, these findings suggest that 15-azaGGSPP and other thiophosphate analogues are likely to be useful as inert, tight-binding active site probes for diterpene cyclases.

Figure 11:
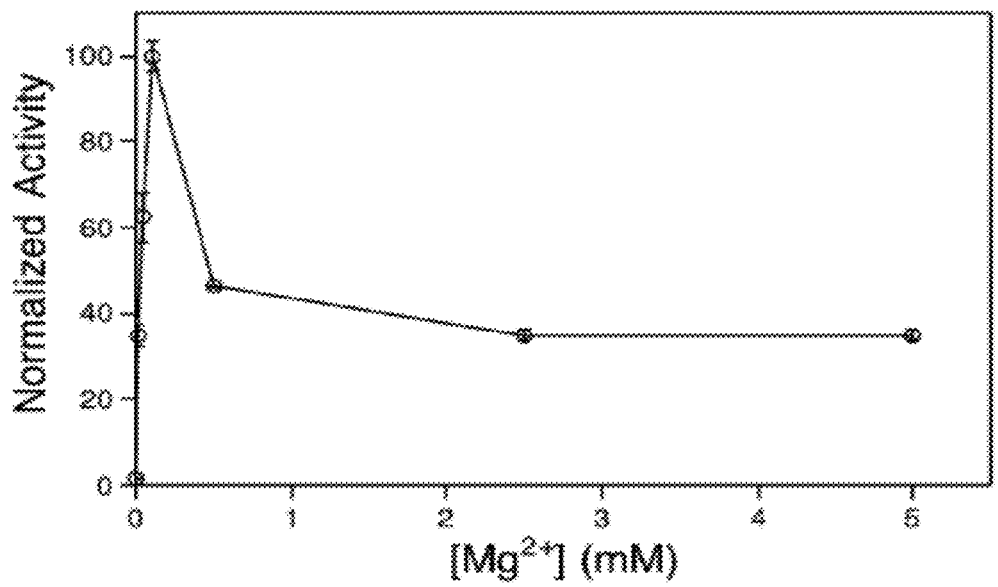
FIG. 11 demonstrates $Mg^{2+}$-dependence of MBP-MtHPS activity.

The kinetic analysis of MtHPS shows a pronounced biphasic dependence on Mg$^{2+}$ levels (FIG. 11). Earlier studies establish that class II diterpene cyclases can exhibit much less susceptibility to Mg$^{2+}$ co-factor inhibition, demonstrating this is not an intrinsic feature of such enzymes. The phagosome appears to be a nutrient-deprived environment, with experiments demonstrating reduced concentrations of various elements in *M. tuberculosis*-containing vacuoles (Wagner et al., *J Immunol.*, 174:1491-1500 (2005)), which have a hypothesized resting Mg$^{2+}$ concentration of 10-50 µM, close to the optimal 100 µM concentration for MtHPS activity. Given that bacterial intracellular concentrations of Mg$^{2+}$ have been demonstrated to reflect that of their external environment, upon endocytic uptake *M tuberculosis* intracellular Mg$^{2+}$ levels would be drastically reduced, leading to increased HPS activity. This should increase flux towards isotuberculosinol production, which then acts to prevent phagosomal maturation.

Figure 14A:
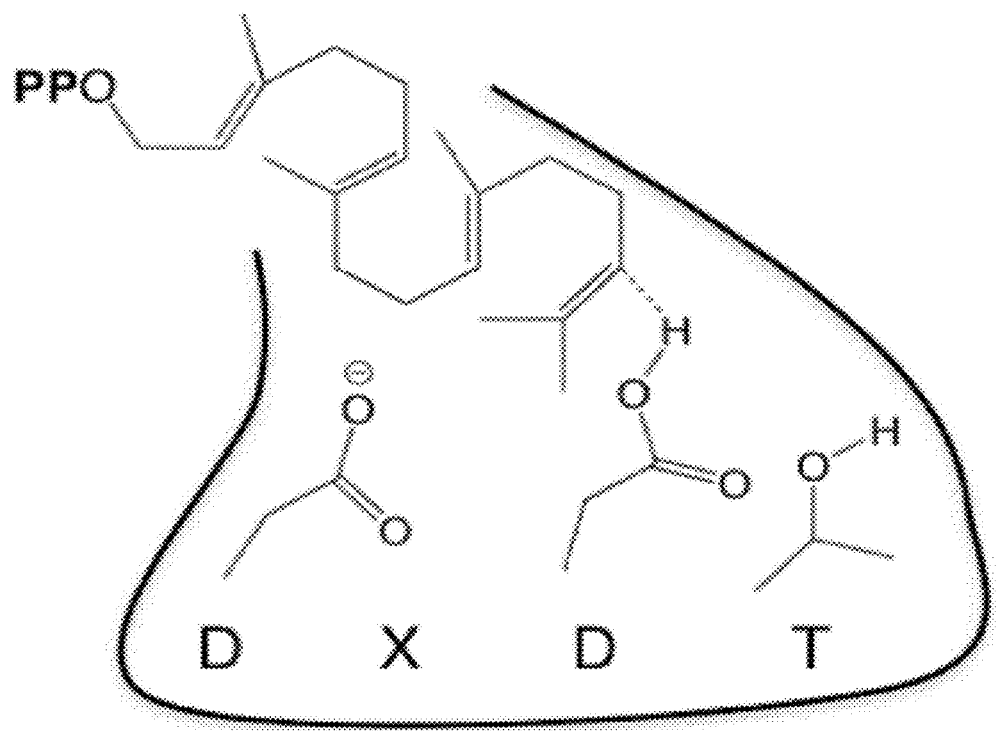
FIGS. 14A-B demonstrate models of DXDT motif in MtHPS active site: (A) as an acid (AH) in productive catalysis; and (B) as an $Mg^{2+}$-binding site, leading to intrasteric inhibition.
Figure 14B:
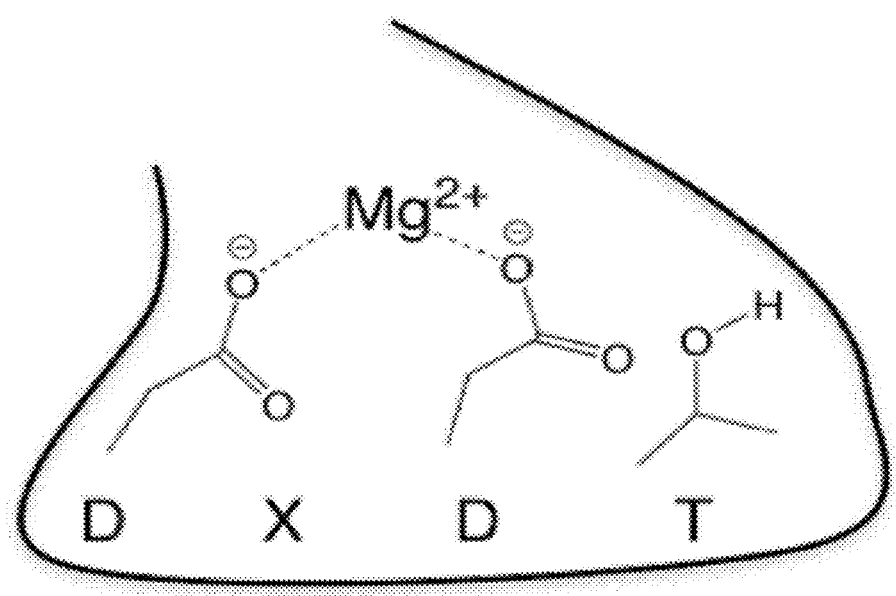

The Mg$^{2+}$ dependence of MtHPS activity represents a physiologically relevant biochemical mechanism that triggers (or at least increases) isotuberculosinol biosynthesis upon phagosomal engulfment. As previously suggested for plant class II diterpene cyclases (Prisic et al. (2007)), the likely site of inhibitory $Mg^{2+}$-binding is the aspartate-rich motif found in such enzymes whose productive role is to synergistically act as the catalytic acid that protonates the terminal carbon-carbon double bond of GGPP, which would provide an example of an intrasteric (i.e., within the active site) inhibitory mechanism. While typically conserved as a DXDD sequence motif, the corresponding sequence was found to be DXDT in MtHPS. Nevertheless, this motif also should be capable of binding $Mg^{2+}$ (FIG. 14).

The classic mechanism-based plant class II diterpene cyclase inhibitor 15-azaGGPP is a very tight binding inhibitor of MtHPS as well. However, 15-azaGGPP contains an easily hydrolyzed diphosphate ester bond. In an initial attempt to modify this inhibitor to increase stability while retaining strong affinity, we substituted the diphosphate ester with a more stable thiolo linkage. The resulting 15-azaGGSPP analog also proved to be a potent inhibitor, indicating that at least such moderate modification to increase stability does not lead to dramatic loss of affinity. Thus, MtHPS and, hence, isotuberculosinol are viable drug target.

All publications and patent applications in this specification are indicative of the level of ordinary skill in the art to which this invention pertains. All publications and patent applications are herein incorporated by reference to the same extent as if each individual publication or patent application was specifically and individually indicated by reference. The disclosure of each reference set forth herein is incorporated herein by reference in its entirety.

The invention has been described with reference to various specific and preferred embodiments and techniques. However, it should be understood that many variations and modifications may be made while remaining within the spirit and scope of the invention.

What is claimed is:

1. A method of identifying compounds which inhibit in vivo infection by *Mycobacterium tuberculosis* comprising:
   providing cells infected with *Mycobacterium tuberculosis* pathogen;
   introducing a compound to said cells; and
   determining whether said compound inhibits MtHPS to arrest synthesis of isotuberculosinol in said pathogen and inhibit *Mycobacterium tuberculosis* replication and infection.

2. The method according to claim 1 wherein said synthesis is enzymatic and encoded by Rv3378c.

3. An assay for identifying drug candidates capable of inhibiting isotuberculosinol synthesis to decrease *Mycobacterium tuberculosis* pathogenicity, comprising:
   providing cells infected with *Mycobacterium tuberculosis* pathogen; and
   administering a drug candidate to said cells to assay for arrest in isotuberculosinol synthesis within *Mycobacterium tuberculosis* pathogen.

4. The assay according to claim 3 wherein said arrest in isotuberculosinol synthesis is caused by an interaction with a class I or II diterpene cyclase.

5. The assay according to claim 3 wherein said synthesis of isotuberculosinol is enzymatic synthesis encoded by Rv3378c.

6. The assay according to claim 3 wherein said drug candidate is a diterpene cyclase antagonist or inhibitor.

7. The assay according to claim 3 wherein $Mg^{2+}$ concentrations in said cells is altered.

8. The assay according to claim 3 wherein said assay tests whether said drug candidate inhibits or enhances the synthesis of isotuberculosinol and wherein said drug candidate is identified as an antagonist or agonist.

* * * * *

UNITED STATES PATENT AND TRADEMARK OFFICE
CERTIFICATE OF CORRECTION

| | |
|---|---|
| PATENT NO. | : 8,309,322 B2 |
| APPLICATION NO. | : 12/776759 |
| DATED | : November 13, 2012 |
| INVENTOR(S) | : Peters et al. |

It is certified that error appears in the above-identified patent and that said Letters Patent is hereby corrected as shown below:

In the specification

Column 1, line 16:

After the word government: delete "may have" and insert --has--.

Signed and Sealed this
Fifteenth Day of March, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,309,322 B2 | Page 1 of 1 |
| APPLICATION NO. | : 12/776759 | |
| DATED | : November 13, 2012 | |
| INVENTOR(S) | : Peters et al. | |

It is certified that error appears in the above-identified patent and that said Letters Patent is hereby corrected as shown below:

Column 1, line 16:

Delete "Work for this invention was funded in part by grants from the National Institute of Health Grant No. GM076324. The United States government has certain rights in this invention." and insert -- This invention was made with government support under GM076324 awarded by National Institutes of Health. The government has certain rights in the invention. --

Signed and Sealed this
Fifth Day of July, 2016

Michelle K. Lee
*Director of the United States Patent and Trademark Office*